US011940450B2

(12) United States Patent
Shapiro et al.

(10) Patent No.: US 11,940,450 B2
(45) Date of Patent: Mar. 26, 2024

(54) BIOMARKER PANEL FOR NON-INVASIVE DIAGNOSIS OF CONGENITAL RENAL DYSFUNCTION

(71) Applicant: UNIVERSITY OF CONNECTICUT, Farmington, CT (US)

(72) Inventors: Linda H. Shapiro, Middlebury, CT (US); Fernando A. Ferrer, Sunny Isles Beach, FL (US); Charan Devarakonda, Vernon, CT (US); James J. Grady, Farmington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 28 days.

(21) Appl. No.: 17/695,381

(22) Filed: Mar. 15, 2022

(65) Prior Publication Data
US 2022/0299530 A1  Sep. 22, 2022

Related U.S. Application Data

(60) Provisional application No. 63/161,601, filed on Mar. 16, 2021.

(51) Int. Cl.
*G01N 33/543* (2006.01)
*G01N 33/68* (2006.01)

(52) U.S. Cl.
CPC ... *G01N 33/6893* (2013.01); *G01N 33/54306* (2013.01); *G01N 2470/06* (2021.08); *G01N 2800/285* (2013.01); *G01N 2800/385* (2013.01); *G01N 2800/50* (2013.01)

(58) Field of Classification Search
None
See application file for complete search history.

(56) References Cited

U.S. PATENT DOCUMENTS

| 10,352,949 | B2 | 7/2019 | Feuerhelm-Heidl et al. | |
|---|---|---|---|---|
| 10,359,433 | B2 | 7/2019 | Turco et al. | |
| 10,365,281 | B2 | 7/2019 | Borgia et al. | |
| 10,365,288 | B2 | 7/2019 | Van Eyk et al. | |
| 2015/0079613 | A1* | 3/2015 | McKnight | A61P 13/12 435/7.92 |
| 2016/0153053 | A1* | 6/2016 | Skog | C12Q 1/6806 435/6.12 |

OTHER PUBLICATIONS

Alizadeh et al., Urinary carbohydrate antigen 19-9/creatinine ratio: a non-invasive marker for follow-up unilateral ureteropelvic junction obstruction in children, Journal of Pediatric Urology, 2018, 14, pp. 62.e1-62.e4. (Year: 2018).*
Taranta-Janusz et al., Is urine intercellular adhesion molecule-1 a marker of renal disorder in children with ureteropelvic junction obstruction, Biomarkers, 2016, 21(2), pp. 123-128). (Year: 2016).*
Torzewski et al., Animal Models of C-Reactive Protein, Hindawl Publishing Corporation, Mediators of Inflammation, vol. 2014, 2014, pp. 1-7. (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Strongin, Laboratory Diagnosis of Viral Infections, Sensitivity, Specificity, and Predictive Value of Diagnostic Tests: Definitions and Clinical applications, Lennette, ed. Marcel Dekker, Inc. New York, pp. 211-219, 1992. (Year: 1992).*
Devarakonda et al., A novel urinary biomarker protein panel to identify children with ureteropelvic junction obstruction—A pilot study , Journal of Peadiatric Urology, Jun. 16, pp. 466.e1-466.e9. (Year: 2020).*
Alizadeh F, Taefnia AM, Haghdani S. Urinary carbohydrate antigen 19-9/creatinine ratio: A non-invasive marker for follow-up of unilateral ureteropelvic junction obstruction in children. J Pediatr Urol. 2018;14(1):62 e61-62 e64.
Belcher, J. M., Edelstein, C. L. & Parikh, C. R. Clinical applications of biomarkers for acute kidney injury. Am J Kidney Dis 57, 930-940, 2010.11.032 (2011).
Chen, H. et al. Quantitative Urinary Proteome Reveals Potential Biomarkers for Ureteropelvic Junction Obstruction. Proteomics Clin Appl 13, e1800101, (2019).
Chevalier RL, Thornhill BA, Forbes MS, Kiley SC. Mechanisms of renal injury and progression of renal disease in congenital obstructive nephropathy. Pediatr Nephrol. 2010;25(4):687-697.
Chevalier RL, Thornhill BA, Wolstenholme JT, Kim A. Unilateral ureteral obstruction in early development alters renal growth: dependence on the duration of obstruction. J Urol. 1999;161(1):309-313.
Chevalier, R. L. Pathogenesis of renal injury in obstructive uropathy. Curr Opin Pediatr 18, 153-160, (2006).
Conway JJ, Maizels M. The "well tempered" diuretic renogram: a standard method to examine the asymptomatic neonate with hydronephrosis or hydroureteronephrosis. A report from combined meetings of The Society for Fetal Urology and members of The Pediatric Nuclear Medicine Council—The Society of Nuclear Medicine. J Nucl Med. 1992;33(11):2047-2051.

(Continued)

*Primary Examiner* — Gary Counts
(74) *Attorney, Agent, or Firm* — McDonnell Boehnen Hulbert & Berghoff LLP

(57) ABSTRACT

Disclosed herein are methods and compositions for prognosing or diagnosing an obstructive renal dysfunction or ureteropelvic junction obstruction (UPJO) in a subject, involving detecting in a urine sample from a subject one or more proteins selected from the group consisting of Immunoglobulin superfamily containing leucine-rich repeat protein (ISLR); Nicotinate-nucleotide pyrophosphorylase [carboxylating] (QPRT); Prostaglandin reductase 1 (PTGR1); Vascular cell adhesion protein 1 (VCAM1); and Ficolin-2 (FCN2), or detectable portions thereof to identify the subject as at risk of or having an obstructive renal dysfunction or UPJO.

11 Claims, 8 Drawing Sheets
Specification includes a Sequence Listing.

(56) References Cited

OTHER PUBLICATIONS

Cost NG, Noh PH, Devarajan P, et al. Urinary NGAL levels correlate with differential renal function in patients with ureteropelvic junction obstruction undergoing pyeloplasty. J Urol. 2013;190(4 Suppl):1462-1467.
Cox J, Mann M. MaxQuant enables high peptide identification rates, individualized p.p.b.-range mass accuracies and proteome-wide protein quantification. Nat Biotechnol. 2008;26(12):1367-1372.
Drube J, Zurbig P, Schiffer E, et al. Urinary proteome analysis identifies infants but not older children requiring pyeloplasty. Pediatr Nephrol. 2010;25(9):1673-1678.
Esmaeili M, Esmaeili M, Ghane F, Alamdaran A. Comparison Between Diuretic Urography (IVP) and Diuretic Renography for Diagnosis of Ureteropelvic Junction Obstruction in Children. Iran J Pediatr. 2016;26(1):e4293.
Forbes MS, Thornhill BA, Minor JJ, Gordon KA, Galarreta CI, Chevalier RL. Fight-or-flight: murine unilateral ureteral obstruction causes extensive proximal tubular degeneration, collecting duct dilatation, and minimal fibrosis. Am J Physiol Renal Physiol. 2012;303(1):F120-129.
Furness, P. D., 3rd, Maizels, M., Han, S. W., Cohn, R. A. & Cheng, E. Y. Elevated bladder urine concentration of transforming growth factor-beta1 correlates with upper urinary tract obstruction in children. J Urol 162, 1033-1036 (1999).
Gerber C, Harel M, Lynch ML, Herbst KW, Ferrer FA, Shapiro LH. Proximal tubule proteins are significantly elevated in bladder urine of patients with ureteropelvic junction obstruction and may represent novel biomarkers: A pilot study. J Pediatr Urol. 2016;12(2):120 e121-127.
Gupta, S. et al. Urinary antimicrobial peptides: Potential novel biomarkers of obstructive uropathy. J Pediatr Urol 14, 238.e231-238.e236, (2018).
Holzscheiter L, Beck C, Rutz S, et al. NGAL, L-FABP, and KIM-1 in comparison to established markers of renal dysfunction. Clin Chem Lab Med. 2014;52(4):537-546.
Kiley, S. C. & Chevalier, R. L. Urinary biomarkers: the future looks promising. Kidney Int 76, 133-134, (2009).
Kim, S. Y. et al. Comparison of the reliability of two hydronephrosis grading systems: The Society for Foetal Urology grading system vs. the Onen grading system. Clin Radiol, 68(9):e484-90 (2013).
Klein J, Gonzalez J, Miravete M, et al. Congenital ureteropelvic junction obstruction: human disease and animal models. Int J Exp Pathol. 2011;92(3):168-192.
Liu KD, Yang W, Anderson AH, et al. Urine neutrophil gelatinase-associated lipocalin levels do not improve risk prediction of progressive chronic kidney disease. Kidney Int. 2013;83(5):909-914.
Madsen, M. G. et al. Urinary NGAL, cystatin C, beta2-microglobulin, and osteopontin significance in hydronephrotic children. Pediatr Nephrol 27, 2099-2106, (2012).
Maeda K, Enomoto A, Hara A, et al. Identification of Meflin as a Potential Marker for Mesenchymal Stromal Cells. Sci Rep. 2016;6:22288.
Martensson, J., Martling, C. R. & Bell, M. Novel biomarkers of acute kidney injury and failure: clinical applicability. Br J Anaesth 109, 843-850, (2012).
Mesrobian HG, Mirza SP. Hydronephrosis: a view from the inside. Pediatr Clin North Am. 2012;59(4):839-851.
Mohammadjafari, H., Rafiei, A., Mousavi, S. A., Alaee, A. & Yeganeh, Y. Role of urinary levels of endothelin-1, monocyte chemotactic peptide-1, and N-acetyl glucosaminidase in predicting the severity of obstruction in hydronephrotic neonates. Korean journal of urology 55, 670-676, (2014).
Nagasawa A, Kubota R, Imamura Y, et al. Cloning of the cDNA for a new member of the immunoglobulin superfamily (ISLR) containing leucine-rich repeat (LRR). Genomics. 1997;44(3):273-279.

Nielsen SE, Andersen S, Zdunek D, Hess G, Parving HH, Rossing P. Tubular markers do not predict the decline in glomerular filtration rate in type 1 diabetic patients with overt nephropathy. Kidney Int. 2011;79(10):1113-1118.
Papachristou, F., Pavlaki, A. & Printza, N. Urinary and serum biomarkers in ureteropelvic junction obstruction: a systematic review. Biomarkers : biochemical indicators of exposure, response, and susceptibility to chemicals 19, 531-540, (2014).
Pavlaki A, Printza N, Farmaki E, et al. The role of urinary NGAL and serum cystatin C in assessing the severity of ureteropelvic junction obstruction in infants. Pediatr Nephrol. 2019 ;35(1):163-170.
Pavlaki, A. et al. Matrix metalloproteinases in ureteropelvic junction obstruction. Hippokratia 21, 136-139 (2017).
Piepsz A. Antenatal detection of pelviureteric junction stenosis: main controversies. Semin Nucl Med. 2011;41 (1):11-19.
Poyan Mehr A, Tran MT, Ralto KM, et al. De novo NAD(+) biosynthetic impairment in acute kidney injury in humans. Nat Med. 2018;24(9):1351-1359.
Ruebner, R. L. et al. Cardiovascular Disease Risk Factors and Left Ventricular Hypertrophy in Girls and Boys With CKD. Clin J Am Soc Nephrol, 7;11(11):1962-1968, (2016).
Sanchez-Rodriguez R, Torres-Mena JE, Quintanar-Jurado V, et al. Ptgr1 expression is regulated by NRF2 in rat hepatocarcinogenesis and promotes cell proliferation and resistance to oxidative stress. Free radical biology & medicine. 2017;102:87-99.
Shirazi, M., Eslahi, A., Sharifi, V., Rahimi, F. & Safarpour, A. Evaluation of Caspase 3 Enzyme and TNF-alpha as Biomarkers in Ureteropelvic Junction Obstruction in Children—a preliminary report. Pakistan journal of medical sciences 33, 315-319, (2017).
Singh S, Wu T, Xie C, et al. Urine VCAM-1 as a marker of renal pathology activity index in lupus nephritis. Arthritis Res Ther. 2012;14(4):R164.
Taha, M. A., Shokeir, A. A., Osman, H. G., Abd el-Aziz Ael, A. & Farahat, S. E. Diagnosis of ureteropelvic junction obstruction in children: role of endothelin-1 in voided urine. Urology 69, 560-564; discussion 564-565, (2007).
Taranta-Janusz, K., Zalewska-Szajda, B., Chojnowska, S. & Wasilewska, A. Urine exoglycosidases are potential markers of renal tubular injury in children with ureteropelvic junction obstruction. Acta Paediatr 104, e518-523, (2015).
Taylor, A. T. Radionuclides in nephrourology, Part 2: pitfalls and diagnostic applications. J Nucl Med 55, 786-798, (2014).
Urbschat A, Gauer S, Paulus P, et al. Serum and urinary NGAL but not KIM-1 raises in human postrenal AKI. Eur J Clin Invest. 2014;44(7):652-659.
Urbschat, A. et al. Serum and urinary NGAL but not KIM-1 raises in human postrenal AKI. Eur J Clin Invest 44, 652-659, (2014).
Wang Y, Gu Y, Loyd S, Jia X, Groome LJ. Increased urinary levels of podocyte glycoproteins, matrix metallopeptidases, inflammatory cytokines, and kidney injury biomarkers in women with preeclampsia. Am J Physiol Renal Physiol. 2015; 309(12):F1009-1017.
Wasilewska A, Taranta-Janusz K, Debek W, Zoch-Zwierz W, Kuroczycka-Saniutycz E. KIM-1 and NGAL: new markers of obstructive nephropathy. Pediatr Nephrol. 2011; 26(4):579-586.
Xue L, Zhu Z, Wang Z, et al. Knockdown of prostaglandin reductase 1 (PTGR1) suppresses prostate cancer cell proliferation by inducing cell cycle arrest and apoptosis. Biosci Trends. 2016;10(2):133-139.
Yang G, Liang Y, Zheng T, et al. FCN2 inhibits epithelial-mesenchymal transition-induced metastasis of hepatocellular carcinoma via TGF-beta/Smad signaling. Cancer letters. 2016; 378(2):80-86.
Yu, L. et al. Elevated urinary lipocalin-2, interleukin-6 and monocyte chemoattractant protein-1 levels in children with congenital ureteropelvic junction obstruction. J Pediatr Urol 15, 44.e41-44.e47, (2019).

* cited by examiner

Figure 1(b)

| Sample | Sex | Age | Weight | Notes |
|---|---|---|---|---|
| Control-1 | M | 10 months | 9.15 kg | Used for mass spectrometric analysis and ELISA |
| Control-2 | M | 9 months | 10 kg | Used for mass spectrometric analysis and ELISA |
| Control-3 | M | 7 months | 7.65 kg | Used for mass spectrometric analysis and ELISA |
| Control-4 | M | 10 months | 7.95 kg | Used for mass spectrometric analysis and ELISA |
| Control-5 | M | 19 months | 11.8 kg | Used for mass spectrometric analysis and ELISA |
| Control-6 | M | 5 months | 6.5 kg | Used for mass spectrometric analysis and ELISA |
| Control-7 | M | 8 months | 9.15 kg | Used for mass spectrometric analysis and ELISA |
| Control-8 | M | 9 months | 8.8 kg | Used for mass spectrometric analysis and ELISA |
| Control-9 | M | 6 months | 7.8 kg | Used for mass spectrometric analysis and ELISA |
| Control-10 | M | 10 months | 8.89 kg | Used for mass spectrometric analysis and ELISA |
| Control-11 | M | 6 months | 7.68 kg | Used for mass spectrometric analysis and ELISA |
| Control-12 | M | 9 months | 8.2 kg | Used for mass spectrometric analysis |
| Control-13 | M | 6 months | 7.8 kg | Used for mass spectrometric analysis and ELISA |
| Control-14 | M | 6 months | 7.7 kg | Used for mass spectrometric analysis and ELISA |
| Control-15 | M | 12 months | 8.3 kg | Used for mass spectrometric analysis and ELISA |
| Control-16 | M | 8 months | 10.1 kg | Used for mass spectrometric analysis and ELISA |
| Control-17 | M | 9 months | 8.8 kg | Used for mass spectrometric analysis and ELISA |
| Control-18 | M | 6 months | 8.5 kg | Used for mass spectrometric analysis and ELISA |
| Control-19 | M | 8 months | 6.2 kg | Used for mass spectrometric analysis and ELISA |
| Control-20 | M | 6 months | 7.9 kg | Used for mass spectrometric analysis and ELISA |
| Control-21 | M | 6 months | 10.3 kg | Used for mass spectrometric analysis and ELISA |
| Control-22 | M | 8 months | 8.9 kg | Used for mass spectrometric analysis and ELISA |
| | | | | |
| UPJO-1 | M | 8 months | 9.15 kg | Used for ELISA |
| UPJO-2 | M | 12 months | 7.75 kg | Used for mass spectrometric analysis and ELISA |
| UPJO-3 | M | 5 months | 7.6 kg | Used for mass spectrometric analysis and ELISA |

| UPJO-4 | M | 3 months | 6.2 kg | Used for mass spectrometric analysis and ELISA |
|---|---|---|---|---|
| UPJO-5 | M | 3 months | 6.2 kg | Used for mass spectrometric analysis and ELISA |
| UPJO-6 | M | 7 months | No info | Used for mass spectrometric analysis |
| UPJO-7 | M | 3 months | No info | Used for mass spectrometric analysis |
| UPJO-8 | M | 15 months | No info | Used for mass spectrometric analysis |
| UPJO-9 | M | 5 months | 7.5 kg | Used for mass spectrometric analysis and ELISA |
| UPJO-10 | M | 2 months | 4.8 kg | Used for mass spectrometric analysis and ELISA |
| UPJO-11 | M | 8 months | 8.1 kg | Used for mass spectrometric analysis and ELISA |
| UPJO-12 | M | 4 months | 5.9 kg | Used for mass spectrometric analysis and ELISA |
| UPJO-13 | M | 4 months | 6.4 kg | Used for mass spectrometric analysis and ELISA |
| UPJO-14 | M | 2 months | 7.65 kg | Used for mass spectrometric analysis and ELISA |
| UPJO-15 | M | 6 weeks | 5.6 kg | Used for mass spectrometric analysis and ELISA |
| UPJO-16 | M | 10 weeks | 6.8 kg | Used for mass spectrometric analysis and ELISA |
| UPJO-17 | M | 10 weeks | 4.89 kg | Used for mass spectrometric analysis and ELISA |
| UPJO-18 | M | 9 months | 9.45 kg | Used for mass spectrometric analysis and ELISA |
| UPJO-19 | M | 7 months | 10.3 kg | Used for mass spectrometric analysis and ELISA |
| UPJO-20 | M | 12 months | 10.8 kg | Used for mass spectrometric analysis and ELISA |
| UPJO-21 | M | 10 months | 5.5 kg | Used for mass spectrometric analysis |
| UPJO-22 | M | 6 months | 7.6 kg | Used for mass spectrometric analysis and ELISA |

| Protein name | Symbol |
|---|---|
| Immunoglobulin superfamily containing leucine-rich repeat protein | ISLR |
| Nicotinate-nucleotide pyrophosphorylase [carboxylating] | QPRT |
| SPARC-like protein 1 | SPARCL1 |
| Fibrinogen gamma chain (Fragment) | FGG |
| Small proline-rich protein 3 | SPRR3 |
| Brain acid soluble protein 1 | BASP1 |
| Prostaglandin reductase 1 | PTGR1 |
| Complement factor H | CFH |
| Vascular cell adhesion protein 1 | VCAM1 |
| Ficolin-2 | FCN2 |
| Neutrophil gelatinase-associated lipocalin | LCN2 |

Figure 2(c)

| UPJO samples with values greater than the Average + 3(SD) value of control samples | | | | | | |
|---|---|---|---|---|---|---|
| Sample | PTGR1 | FCN2 | QPRT | ISLR | VCAM1 | % Positive proteins |
| UPJO-1 | × | × | × | × | × | (0/5) 0% |
| UPJO-2 | Yes | Yes | × | × | × | (2/5) 40% |
| UPJO-3 | Yes | Yes | × | × | × | (2/5) 40% |
| UPJO-4 | Yes | Yes | Yes | × | × | (3/5) 60% |
| UPJO-5 | × | × | Yes | × | × | (1/5) 40% |
| UPJO-9 | Yes | Yes | × | × | × | (2/5) 40% |
| UPJO-10 | Yes | Yes | Yes | Yes | Yes | (5/5) 100% |
| UPJO-11 | Yes | Yes | × | × | × | (2/5) 40% |
| UPJO-12 | Yes | × | Yes | × | Yes | (3/5) 60% |
| UPJO-13 | Yes | Yes | × | × | × | (2/5) 40% |
| UPJO-14 | Yes | Yes | Yes | × | × | (3/5) 60% |
| UPJO-15 | Yes | × | Yes | Yes | × | (3/5) 60% |
| UPJO-16 | Yes | × | Yes | Yes | × | (3/5) 60% |
| UPJO-17 | Yes | × | Yes | × | × | (2/5) 40% |
| UPJO-18 | Yes | Yes | Yes | Yes | Yes | (5/5) 100% |
| UPJO-19 | Yes | Yes | × | × | × | (2/5) 40% |
| UPJO-20 | Yes | Yes | × | × | × | (2/5) 40% |
| UPJO-22 | Yes | Yes | Yes | Yes | Yes | (5/5) 100% |
| Positive samples (%) | 16/18 (88.89%) | 12/18 (66.67%) | 10/18 (55.56%) | 5/18 (27.78%) | 4/18 (22.22%) | |

Figure 2(d)

| Positive samples (%) | | | | |
|---|---|---|---|---|
| | Average + 3(SD) | | Average + 4(SD) | |
| | Control | UPJO | Control | UPJO |
| PTGR1 | 5.56 | 88.89 | 0.00 | 83.33 |
| FCN2 | 0.00 | 66.67 | 0.00 | 44.44 |
| QPRT | 5.00 | 55.56 | 0.00 | 44.44 |
| ISLR | 0.00 | 27.78 | 0.00 | 27.78 |
| VCAM1 | 0.00 | 22.22 | 0.00 | 22.22 |

BIOMARKER PANEL FOR NON-INVASIVE DIAGNOSIS OF CONGENITAL RENAL DYSFUNCTION

CROSS REFERENCE

This application claims priority to U.S. Provisional Application Ser. No. 63/161,601 filed Mar. 16, 2021, incorporated by reference herein in its entirety.

STATEMENT OF GOVERNMENT SUPPORT

This invention was made with government support under Grant No.HL127449 from the National Institutes of Health. The government has certain rights in the invention.

SEQUENCE LISTING STATEMENT

A computer readable form of the Sequence Listing is filed with this application by electronic submission and is incorporated into this application by reference in its entirety. The Sequence Listing is contained in the file created on March 14, 2022 having the file name "22-0360-US-SeqList_ST25.txt" and is 21 kb in size.

FIELD OF DISCLOSURE

The disclosure contained herein is in the general field of identification of people with congenital renal dysfunction, including children with obstructive renal dysfunction, such as resulting from ureteropelvic junction obstruction (UPJO).

BACKGROUND

Ureteropelvic junction obstruction (UPJO) is one of the obstructive congenital anomalies of the kidney and urinary tract (CAKUT) and represents the most common cause of chronic kidney disease in children. Advances in maternal sonography have improved early detection of UPJO, however hydronephrosis does not necessarily equate to obstruction. While surgical intervention is successful when nuclear medicine studies confirm obstruction, these studies are invasive. In some situations, a 'watchful waiting' approach is adopted for asymptomatic infants, entailing periodic assessment of function by radiotracer-extraction studies that are cumbersome and often are equivocal. Current therapeutic goals focus on halting progressive injury and enhancing subsequent healing. However, progress in these areas is severely hampered by the paucity of reliable biomarkers to assess the effects of obstruction.

SUMMARY

In one aspect, the disclosure provides methods for prognosing or diagnosing an obstructive renal dysfunction in a subject, comprising:
  (a) detecting in a urine sample from a subject one or more proteins selected from the group consisting of Immunoglobulin superfamily containing leucine-rich repeat protein (ISLR); Nicotinate-nucleotide pyrophosphorylase [carboxylating] (QPRT); Prostaglandin reductase 1 (PTGR1); Vascular cell adhesion protein 1 (VCAM1); and Ficolin-2 (FCN2), or detectable portions thereof; and
  (b) comparing an amount of the one or more proteins in the urine sample to a standard;
  wherein an amount of at least one of the one or more proteins in the urine sample above the standard identifies the subject as at risk of or having an obstructive renal dysfunction.

In one embodiment, an amount of at least one of the one or more proteins in the urine sample above the standard identifies the subject as at risk of or having an obstructive renal dysfunction resulting from ureteropelvic junction obstruction (UPJO).

In one embodiment, wherein the detecting comprises contacting the urine sample with antibodies that bind to the one or more proteins, and detecting binding of the antibodies to the one or more proteins. In another embodiment, the method comprises identifying the subject as having an obstructive renal dysfunction or UPJO, and wherein the method further comprises treating the subject for the obstructive renal dysfunction or UPJO.

In another aspect, the disclosure provides compositions, comprising antibodies that specifically bind 2, 3, 4, or all 5 proteins selected from the group consisting of ISLR, QPRT, PTGR1, VCAM1, and FCN2, or antigen binding portions thereof. In one embodiment, the antibodies are immobilized on a surface of a solid support. In another embodiment, the antibodies are detectably labeled, such as fluorescently labeled, radioactively labeled, or colorimetrically labeled.

DETAILED DESCRIPTION

Figure 1:
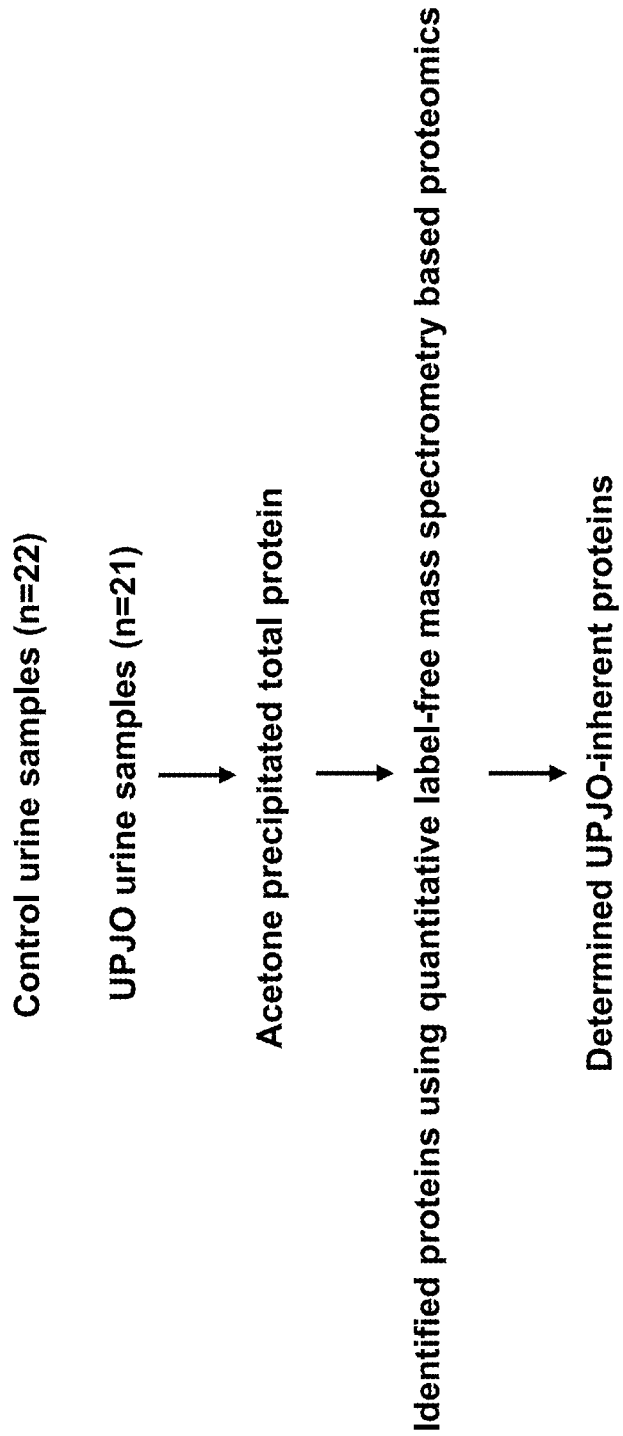
FIG. 1(A-C). Mass spectrometric identification of 10 candidate biomarker proteins present in UPJO but absent in control patients. (A) Methodology employed to identify UPJO-inherent urinary proteins. (B) Odds ratio analysis of top 10 UPJO-inherent urinary proteins identified by mass spectrometry analysis. Average precursor intensities of individual proteins was used to stratify control and UPJO samples according to the presence or absence of candidate proteins. Odds ratio was calculated for each protein as shown in the table. LCN2 was included for comparative analysis. (C) List of the top ten ranked biomarker proteins.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, CA), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, CA), *Culture of Animal Cells: A Manual of Basic Technique*, $2^{nd}$ Ed. (R. I. Freshney. 1987. Liss, Inc. New York, NY), and *Gene Transfer and Expression Protocols*, pp. 109-128, ed. E. J. Murray, The Humana Press Inc., Clifton, N.J.

As used herein, the singular forms "a", "an" and "the" include plural referents unless the context clearly dictates otherwise. "And" as used herein is interchangeably used with "or" unless expressly stated otherwise.

All embodiments of any aspect of the disclosure can be used in combination, unless the context clearly dictates otherwise.

Disclosed herein is a panel of biomarkers that are can be used to prognose or diagnose obstructive renal dysfunction and improve upon current detection methods.

It is an object of the disclosed panel and methods associated with it that clinicians and clinical laboratories will use this panel to non-invasively and cost-effectively identify subjects, including but not limited to infants and children with obstructive dysfunction.

In one aspect, the disclosure provides method for prognosing or diagnosing obstructive renal dysfunction in a subject, comprising:
(a) detecting in a urine sample from a subject one or more proteins selected from the group consisting of Immunoglobulin superfamily containing leucine-rich repeat protein (ISLR); Nicotinate-nucleotide pyrophosphorylase [carboxylating] (QPRT); Prostaglandin reductase 1 (PTGR1); Vascular cell adhesion protein 1 (VCAM1); and Ficolin-2 (FCN2), or detectable portions thereof; and
(b) comparing an amount of the one or more proteins in the urine sample to a standard;
wherein an amount of at least one of the one or more proteins in the urine sample above the standard identifies the subject as at risk of or having an obstructive renal dysfunction.

The methods may be used to prognose or diagnose any obstructive renal dysfunction. An obstructive renal dysfunction is any condition in which a ureteral blockage obstructs the normal passage of urine to the bladder, leading to accumulation of urine into one or both kidneys, causing detrimental swelling and stretching. In congenital ureteral obstruction, partial or complete obstruction of one or both of the ureters prevents or impedes the flow of urine into the bladder from the kidney. An early effect of ureteral obstruction is an increase in pressure in the proximal tubules causing distention, damage and shedding of proteins expressed on the apical surface of the proximal tubular brush border epithelium into the urine. In its most severe form, urinary tract obstruction can lead to prenatal or early infant death. Other children may progress to develop chronic kidney disease and kidney failure requiring lifelong monitoring and renal replacement therapy. Moreover, all of these patients are at a greater risk of developing early cardiovascular disease. The severity and location of the obstruction and the timing of its relief affect outcomes; current therapeutic goals focus on halting progressive injury and enhancing subsequent healing.

In various non-limiting embodiments, the obstructive renal dysfunction results from ureteropelvic junction obstruction (UPJO), Vesicoureteral Reflux (VUR), Ureterovesical Junction Obstruction (UVJ), posterior ureteral valves (PUV), ureterocele, or ectopic ureter. Each of these conditions interferes with normal urine flow from the kidney to the bladder. UPJO refers to a blockage in the area that connects the renal pelvis (part of the kidney) to one of the tubes (ureters) that move urine to the bladder. VUR occurs when one or both ureters are not positioned appropriately or have poor muscle connections to the bladder. UVJ is a distinct type of blockage in the area where the ureter meets the bladder; PUV are leaflets, or extra flaps of tissue, that develop in the male urethra that impede urine flow and bladder emptying; ureterocele blockage in one or more of the ureters, preventing the normal flow of urine. A ureterocele is a balloon-like blockage of the ureter closer to the bladder; ectopic ureter refers to the condition where the connection between the ureter and the bladder does not form properly and drains somewhere outside of the bladder. These congenital anomalies of the kidney and urinary tract (CAKUT) occur in 1 in 100 to 500 newborns, can be severe and lead to lead to chronic kidney disease and hypertension, which can affect a child's growth and development, requiring lifetime monitoring. CAKUT patients are also at a greater risk for cardiovascular disease. Surgery is needed in cases of compromised kidney function.

In one non-limiting embodiment, the obstructive renal dysfunction results from UPJO.

The subject may be any subject at risk of having obstructive renal dysfunction. In one embodiment, the subject is a mammal, such as a human subject. In another non-limiting embodiment, the subject may be a child (i.e.: less than 18 years of age); in another embodiment, the subject may be an infant or young child (i.e.: under the age of 3 years old, or under the age of three years old). In another embodiment, the subject is a male subject.

In one embodiment, a subject at risk of having obstructive renal dysfunction (including but not limited to UPJO) may be one presenting with one or more symptoms selected from back or flank pain, bloody urine (hematuria), lump in the abdomen (abdominal mass), kidney infection, poor growth in infants (failure to thrive), urinary tract infection, usually with fever, and/or vomiting.

Any standard may be used as deemed suitable by attending medical personnel. In one embodiment, the standard comprises a normal range determined from subjects not having an obstructive renal dysfunction. In this embodiment, the normal range may be a predetermined range used for comparison to the amount determined in the subject. In another embodiment, the standard may comprise a normal range determined from subjects not having UPJO. In these embodiments, an amount of at least one of the one or more proteins in the urine sample above the standard identifies the subject as at risk of or having an obstructive renal dysfunction.

Any amount of the one or more proteins above standard may identify the subject as at risk of or having an obstructive renal dysfunction. In various embodiments, an amount of the one or more proteins 10%, 20%, 30%, 40%, 50%, 60%, 70%, 80%, 90%, 100%, or more above standard may identify the subject as at risk of or having an obstructive renal dysfunction. In another embodiment, the standard may be that none of the one or more proteins are detectable in normal urine, and thus any amount of the one or more proteins may identify the subject as at risk of or having an obstructive renal dysfunction.

In various embodiments, an amount of at least 2, 3, 4, or all 5 of the one or more proteins in the urine sample above the standard identifies the subject as at risk of or having an obstructive renal dysfunction. In one embodiment, an amount of PTGR1 in the urine sample above the standard identifies the subject as at risk of or having an obstructive renal dysfunction. In another embodiment, an amount of PTGR1 and FCN2 in the urine sample above the standard identifies the subject as at risk of or having an obstructive renal dysfunction. In a further embodiment, an amount of PTGR1, FCN2, and QPRT in the urine sample above the standard identifies the subject as at risk of or having an obstructive renal dysfunction. In one embodiment, an amount of PTGR1, FCN2, QPRT, and ISLR in the urine sample above the standard identifies the subject as at risk of or having an obstructive renal dysfunction.

Urine samples may be obtained and processed (though processing is not required) from the subject using standard techniques. The protein markers, or detectable portions thereof can be detected in the urine samples using standard techniques. As will be understood by those of skill in the art, the specific amino acid sequence of the markers in different subjects may differ. In various non-limiting embodiments, the one or more proteins in the urine sample, or detectable portions thereof, have an amino acid sequence at least 75%, 80%, 85%, 90%, 91%, 92%, 93%, 94%, 95%, 96%, 97%, 98%, 99%, or 100% identical to the amino acid sequence of one or more of SEQ ID NOS:1-5, or detectable portions thereof. As will be understood by those of skill in the art, the proteins in the urine may have undergone degradation, proteolytic cleavage, etc., and thus the methods comprise detecting detectable portions of the proteins.

```
ISLR UniProtKB - Q6UXK2
>sp|Q6UXK2|ISLR2 HUMAN Immunoglobulin superfamily containing leucine-rich
repeat protein 2 OS = Homo sapiens OX = 9606 GN = ISLR2 PE = 1 SV = 1
                                                             (SEQ ID NO: 1)
MFPLRALWLVWALLGVAGSCPEPCACVDKYAHQFADCAYKELREVPEGLPANVTTLSLSA

NKITVLRRGAFADVTQVTSLWLAHNEVRTVEPGALAVLSQLKNLDLSHNFISSFPWSDLR

NLSALQLLKMNHNRLGSLPRDALGALPDLRSLRINNNRLRTLAPGTFDALSALSHLQLYH

NPFHCGCGLVWLQAWAASTRVSLPEPDSIACASPPALQGVPVYRLPALPCAPPSVHLSAE

PPLEAPGTPLRAGLAFVLHCIADGHPTPRLQWQLQIPGGTVVLEPPVLSGEDDGVGAEEG

EGEGDGDLLTQTQAQTPTPAPAWPAPPATPRFLALANGSLLVPLLSAKEAGVYTCRAHNE

LGANSTSIRVAVAATGPPKHAPGAGGEPDGQAPTSERKSTAKGRGNSVLPSKPEGKIKGQ

GLAKVSILGETETEPEEDTSEGEEAEDQILADPAEEQRCGNGDPSRYVSNHAFNQSAELK

PHVFELGVIALDVAEREARVQLTPLAARWGPGPGGAGGAPRPGRRPLRLLYLCPAGGGAA

VQWSRVEEGVNAYWERGLRPGTNYSVCLALAGEACHVQVVESTKKELPSLLVIVAVSVFL

LVLATVPLLGAACCHLLAKHPGKPYRLILRPQAPDPMEKRIAADFDPRASYLESEKSYPA

GGEAGGEEPEDVQGEGLDEDAEQGDPSGDLQREESLAACSLVESQSKANQEEFEAGSEYS

DRLPLGAEAVNIAQEINGNYRQTAG

QPRT: UniProtKB - Q15274
>sp|Q15274|NADC_HUMAN Nicotinate-nucleotide pyrophosphorylase [carboxylating]
OS = Homo sapiens OX = 9606 GN = QPRT PE = 1 SV = 3
                                                             (SEQ ID NO: 2)
MDAEGLALLLPPVTLAALVDSWLREDCPGLNYAALVSGAGPSQAALWAKSPGVLAGQPFF

DAIFTQLNCQVSWFLPEGSKLVPVARVAEVRGPAHCLLLGERVALNTLARCSGIASAAAA

AVEAARGAGWTGHVAGTRKTTPGFRLVEKYGLLVGGAASHRYDLGGLVMVKDNHVVAAGG

VEKAVRAARQAADFTLKVEVECSSLQEAVQAAEAGADLVLLDNFKPEELHPTATVLKAQF

PSVAVEASGGITLDNLPQFCGPHIDVISMGMLTQAAPALDFSLKLFAKEVAPVPKIH
```

-continued

```
PTGR1: UniProtKB - Q14914
sp|Q14914|PTGR1_HUMAN Prostaglandin reductase 1 OS = Homo sapiens OX = 9606
GN = PTGR1 PE = 1 SV = 2
                                                                (SEQ ID NO: 3)
MVRTKTWTLKKHFVGYPTNSDFELKTAELPPLKNGEVLLEALFLTVDPYMRVAAKRLKEG

DTMMGQQVAKVVESKNVALPKGTIVLASPGWTTHSISDGKDLEKLLTEWPDTIPLSLALG

TVGMPGLTAYEGLLEICGVKGGETVMVNAAAGAVGSVVGQIAKLKGCKVVGAVGSDEKVA

YLQKLGFDVVFNYKTVESLEETLKKASPDGYDCYFDNVGGEFSNTVIGQMKKFGRIAICG

AISTYNRTGPLPPGPPPEIVIYQELRMEAFVVYRWQGDARQKALKDLLKWVLEGKIQYKE

YIIEGFENMPAAFMGMLKGDNLGKTIVKA

VCAM1: UniProtKB - P19320
>sp|P19320|VCAM1_HUMAN Vascular cell adhesion protein 1 OS = Homo sapiens
OX = 9606 GN = VCAM1 PE = 1 SV = 1
                                                                (SEQ ID NO: 4)
MPGKMVVILGASNILWIMFAASQAFKIETTPESRYLAQIGDSVSLTCSTTGCESPFFSWR

TQIDSPLNGKVTNEGTTSTLTMNPVSFGNEHSYLCTATCESRKLEKGIQVEIYSFPKDPE

IHLSGPLEAGKPITVKCSVADVYPFDRLEIDLLKGDHLMKSQEFLEDADRKSLETKSLEV

TFTPVIEDIGKVLVCRAKLHIDEMDSVPTVRQAVKELQVYISPKNTVISVNPSTKLQEGG

SVTMTCSSEGLPAPEIEWSKKLDNGNLQHLSGNATLTLIAMRMEDSGIYVCEGVNLIGKN

RKEVELIVQEKPFTVEISPGPRIAAQIGDSVMLTCSVMGCESPSFSWRTQIDSPLSGKVR

SEGTNSTLTLSPVSFENEHSYLCTVTCGHKKLEKGIQVELYSFPRDPEIEMSGGLVNGSS

VTVSCKVPSVYPLDRLEIELLKGETILENIEFLEDTDMKSLENKSLEMTFIPTIEDTGKA

LVCQAKLHIDDMEFEPKQRQSTQTLYVNVAPRDTTVLVSPSSILEEGSSVNMTCLSQGFP

APKILWSRQLPNGELQPLSENATLTLISTKMEDSGVYLCEGINQAGRSRKEVELIIQVTP

KDIKLTAFPSESVKEGDTVIISCTCGNVPETWIILKKKAETGDTVLKSIDGAYTIRKAQL

KDAGVYECESKNKVGSQLRSLTLDVQGRENNKDYFSPELLVLYFASSLIIPAIGMITYFA

RKANMKGSYSLVEAQKSKV

FCN2: UniProdKB - Q15485
>sp|Q15485|FCN2_HUMAN Ficolin-2 OS = Homo sapiens OX = 9606 GN = FCN2 PE = 1 SV = 2
                                                                (SEQ ID NO: 5)
MELDRAVGVLGAATLLLSFLGMAWALQAADTCPEVKMVGLEGSDKLTILRGCPGLPGAPG

PKGEAGTNGKRGERGPPGPPGKAGPPGPNGAPGEPQPCLTGPRTCKDLLDRGHFLSGWHT

IYLPDCRPLTVLCDMDTDGGGWTVFQRRVDGSVDFYRDWATYKQGFGSRLGEFWLGNDNI

HALTAQGTSELRVDLVDFEDNYQFAKYRSFKVADEAEKYNLVLGAFVEGSAGDSLTFHNN

QSFSTKDQDNDLNTGNCAVMFQGAWWYKNCHVSNLNGRYLRGTHGSFANGINWKSGKGYN

YSYKVSEMKVRPA
```

Detecting the presence of the protein markers can be carried out using any suitable techniques. In various non-limiting embodiments, the detecting may comprise use of mass spectroscopy or Western blotting to detect the one or more proteins present in the urine sample. In another embodiment, the detecting comprises use of antibodies to detect the one or more proteins. In some embodiments, the methods may comprise using (for each protein marker to be detected) a single antibody that specifically binds to a single one of the protein markers, or may comprise using a plurality (2, 3, 4, 5, or more) of antibodies that each specifically bind to the same protein marker, but bind to different epitopes on the protein marker. This latter embodiment may be particularly useful if the protein may be be partially degraded in the urine sample. In one such embodiment, an enzyme-linked immunosorbent assay (ELISA) is used. ELISAs can be carried out using standard techniques and antibodies that selectively bind to the one or more proteins. In one embodiment, a sandwich ELISA can be used in which two antibodies that recognize different epitopes of the same protein are used, one as the 'capture antibody' that is fixed to a solid surface such as a plate or well, and the second is the 'detecting antibody' that is labeled with an detectable label (fluorescent, radioactive, colorimetric, etc.)

In another embodiment, the method comprises identifying the subject as having an obstructive renal dysfunction, and wherein the method further comprises treating the subject for the obstructive renal dysfunction. In a further embodiment, the method comprises identifying the subject as having UPJO, and wherein the method further comprises treating the subject for UPJO.

The traditional treatment for UPJO has been open surgery to cut out the area of scarring and re-connect the ureter to the kidney. Over the past several years, newer less invasive treatment options have been developed. Endopyelotomy is a procedure through which a telescope or balloon with an electric wire on it is passed to the level of the kidney. The scar tissue is then cut open from the inside. These procedures can be done in a short period of time as an outpatient with minimal anesthetic and with a much shorter recuperation than with open surgery. Patients will have to keep a temporary internal tube (stent) for four to six weeks. The radiographic success rate with these procedures are 15%-20% lower than what is obtained with open surgery. Moreover, 40% of patients may have significant persistent pain following procedure. Laparoscopic pyeloplasty was developed in order to give the same high success rate obtained with open pyeloplasty while decreasing the morbidity. The internal procedure is performed in the same manner as the open surgery without the need for a large incision. Postoperative pain is less, recuperation is significantly quicker and scarring is minimal when compared with open surgery. The procedure requires a general anesthetic and hospitalization (usually 2 nights). An internal stent is also needed for four weeks. Success with this procedure is the same as open surgery (>95%).

Congenital obstructive renal anomalies are one of the most common causes of renal replacement therapies in children. Timely diagnosis and intervention can circumvent these consequences. Current diagnostic techniques are invasive, costly and imprecise. This diagnostic panel would replace current diagnostic modalities in a simple, non-invasive, cost-effective urine test.

The methods may also be used to assess efficacy of a therapeutic treatment for obstructive renal dysfunction or UPJO. In one embodiment, the methods further comprise;
(a) detecting one or more proteins selected from the group consisting of ISLR, QPRT, PTGR1, VCAM1, and FCN2, or detectable portions thereof, in a urine sample from a subject that has undergone treatment for the obstructive renal dysfunction or UPJO; and
(b) comparing an amount of the one or more proteins in the urine sample to a standard;
wherein a decrease in the amount of the or more (1, 2, 3, 4, or all 5) proteins in the urine sample relative to the standard indicates the treatment was effective; or
wherein no change or an increase in the amount of the one or more (1, 2, 3, 4, or all 5) proteins in the urine sample relative to the standard indicates the treatment was ineffective.

In this embodiment, the standard will typically be an amount of the one or more proteins in an earlier urine sample from the subject, prior to the treatment. In this embodiment, if no change or an increase in the amount of the one or more proteins in the urine sample relative to the standard indicates the treatment was ineffective, and wherein the method further comprises administering a further treatment to the subject to treat the obstructive renal dysfunction or UPJO.

In another aspect, the disclosure provides compositions, comprising antibodies that specifically bind 2, 3, 4, or all 5 proteins selected from the group consisting of ISLR, QPRT, PTGR1, VCAM1, and FCN2, or antigen binding portions thereof. The compositions can be used, for example, in the diagnostic and prognostic methods of the disclosure. In one embodiment, the composition comprises antibodies that specifically bind PTGR1, or antigen binding portions thereof. In another embodiment, the composition comprises antibodies that specifically bind FCN2, or antigen binding portions thereof. In a further embodiment, the composition comprises antibodies that specifically bind QPRT, or antigen binding portions thereof.

In one embodiment, the composition comprises
(a) antibodies that specifically bind PTGR1, or antigen binding portions thereof; and
(b) antibodies that specifically bind FCN2, or antigen binding portions thereof.

In another embodiment, the composition comprises
(a) antibodies that specifically bind PTGR1, or antigen binding portions thereof;
(b) antibodies that specifically bind FCN2, or antigen binding portions thereof; and
(c) antibodies that specifically bind QPRT, or antigen binding portions thereof.

In a further embodiment, the composition comprises antibodies that specifically bind ISLR, or antigen binding portions thereof. In another embodiment, the composition comprises antibodies that specifically bind VCAM1, or antigen binding portions thereof.

In one embodiment, the composition comprises
(a) antibodies that specifically bind PTGR1, or antigen binding portions thereof;
(b) antibodies that specifically bind FCN2, or antigen binding portions thereof;
(c) antibodies that specifically bind QPRT, or antigen binding portions thereof;
(d) antibodies that specifically bind ISLR, or antigen binding portions thereof; and
(e) antibodies that specifically bind VCAM1, or antigen binding portions thereof.

The compositions can be stored frozen, in lyophilized form, or as a solution. In one embodiment, the peptides may be immobilized on a surface of a solid support. Any suitable solid support may be used. Examples of such supports include, but are not limited to, microarrays, beads, columns, optical fibers, wipes, nitrocellulose, nylon, glass, quartz, diazotized membranes (paper or nylon), silicones, polyformaldehyde, cellulose, cellulose acetate, paper, ceramics, metals, metalloids, semiconductive materials, coated beads, magnetic particles; plastics such as polyethylene, polypropylene, and polystyrene; and gel-forming materials, such as proteins (e.g., gelatins), lipopolysaccharides, silicates, agarose, polyacrylamides, methylmethracrylate polymers; sol gels; porous polymer hydrogels; nanostructured surfaces; nanotubes (such as carbon nanotubes), and nanoparticles (such as gold nanoparticles or quantum dots). This embodiment facilitates use of the compositions in various detection assays.

In a specific embodiment, the composition comprises capture antibodies that specifically bind the one or more proteins are directly adsorbed on plastic (such as polystyrene) and modified with an avidin-biotin system to increase antigen capture in detection assays, such as ELISAs. Adsorption of proteins on polystyrene is noncovalent and proportional to the amount added for up to 150 ng/200 microliter in a microtiter well.

In another embodiment, the antibodies may be labeled with a detectable label. Any suitable detectable label can be used, including but not limited fluorescent, radioactive, or colorimetric labels. In one embodiment, the detectable labels for each antibody type are detectable distinguishable. Methods for detecting the label include, but are not limited to spectroscopic, photochemical, biochemical, immunochemical, physical or chemical techniques.

All documents cited herein are expressly incorporated herein in their entirety to the same extent as if each document or cited publication/patent document was individually and expressly incorporated herein:

While the invention has been described with reference to preferred embodiments, it will be understood by those skilled in the art that various changes may be made and equivalents may be substituted for the elements thereof without departing from the scope of the invention. In addition, many modifications may be made to adapt the teaching of the invention to particular use, application, manufacturing conditions, use conditions, composition, medium, size, and/ or materials without departing from the essential scope and spirit of the invention. Therefore, it is intended that the invention not be limited to the particular embodiments and best mode contemplated for carrying out this invention as described herein. Since many modifications, variations, and changes in detail can be made to the described examples, it is intended that all matters in the preceding description and shown in the accompanying figures be interpreted as illustrative and not in a limiting sense.

All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and words of a similar nature in the context of describing the improvements disclosed herein are to be construed to cover both the singular and the plural, unless otherwise indicated herein or clearly contradicted by context. Further, it should further be noted that the terms "first," "second," and the like herein do not denote any order, quantity, or relative importance, but rather are used to distinguish one element from another.

All methods described herein can be performed in any suitable order unless otherwise indicated herein or otherwise clearly contradicted by context. The use of any and all examples, or exemplary language (e.g., "such as"), is intended merely to better illustrate the invention and does not pose a limitation on the scope of the invention or any embodiments unless otherwise claimed.

EXAMPLES

Abstract

Reliable urinary biomarker proteins would be invaluable in identifying children with ureteropelvic junction obstruction (UPJO); to this end, total protein from control (n=22) and UPJO (n=21) urine samples was analyzed by mass spectrometry and candidate biomarker proteins were ranked according to their diagnostic odds ratio. The top ten proteins with highest odds ratio were tested by ELISA and normalized to urine creatinine levels. Five of the 10 proteins — prostaglandin-reductase-1, ficolin-2, nicotinate-nucleotide pyrophosphorylase [carboxylating], immunoglobulin superfamily-containing leucine-rich-repeat-protein and vascular cell adhesion molecule-1 were present at higher levels in the UPJO samples and emerged as a panel of biomarkers to identify obstructive uropathy.

In this study, we implemented quantitative label-free mass spectrometry-based proteomics analysis of UPJO patient and control urine samples to identify proteins that are preferentially present in UPJO patients (UPJO-inherent). We validated these findings with ELISA and generated a panel of 5 biomarker proteins (PTGR1, FCN2, QPRT, ISLR and VCAM1) that form a UPJO-inherent signature.

Results

Identification of UPJO-Inherent Candidate Biomarker Proteins

To minimize initial variability in the urine-proteome, age-restricted (<2 years) and gender-matched cohort of UPJO patients (n=21) and hypospadias repair controls (n=22) were selected (FIG. 1a and Table 1).

TABLE 1

Control and UPJO patient characteristics

| Sample | Sex | Age | Weight | Notes |
|---|---|---|---|---|
| Control-1 | M | 10 months | 9.15 kg | Used for mass spectrometric analysis and ELISA |
| Control-2 | M | 9 months | 10 kg | Used for mass spectrometric analysis and ELISA |
| Control-3 | M | 7 months | 7.65 kg | Used for mass spectrometric analysis and ELISA |
| Control-4 | M | 10 months | 7.95 kg | Used for mass spectrometric analysis and ELISA |
| Control-5 | M | 19 months | 11.8 kg | Used for mass spectrometric analysis and ELISA |
| Control-6 | M | 5 months | 6.5 kg | Used for mass spectrometric analysis and ELISA |
| Control-7 | M | 8 months | 9.15 kg | Used for mass spectrometric analysis and ELISA |
| Control-8 | M | 9 months | 8.8 kg | Used for mass spectrometric analysis and ELISA |
| Control-9 | M | 6 months | 7.8 kg | Used for mass spectrometric analysis and ELISA |
| Control-10 | M | 10 months | 8.89 kg | Used for mass spectrometric analysis and ELISA |
| Control-11 | M | 6 months | 7.68 kg | Used for mass spectrometric analysis and ELISA |
| Control-12 | M | 9 months | 8.2 kg | Used for mass spectrometric analysis |
| Control-13 | M | 6 months | 7.8 kg | Used for mass spectrometric analysis and ELISA |
| Control-14 | M | 6 months | 7.7 kg | Used for mass spectrometric analysis and ELISA |
| Control-15 | M | 12 months | 8.3 kg | Used for mass spectrometric analysis and ELISA |
| Control-16 | M | 8 months | 10.1 kg | Used for mass spectrometric analysis and ELISA |
| Control-17 | M | 9 months | 8.8 kg | Used for mass spectrometric analysis and ELISA |
| Control-18 | M | 6 months | 8.5 kg | Used for mass spectrometric analysis and ELISA |
| Control-19 | M | 8 months | 6.2 kg | Used for mass spectrometric analysis and ELISA |
| Control-20 | M | 6 months | 7.9 kg | Used for mass spectrometric analysis and ELISA |
| Control-21 | M | 6 months | 10.3 kg | Used for mass spectrometric analysis and ELISA |
| Control-22 | M | 8 months | 8.9 kg | Used for mass spectrometric analysis and ELISA |
| UPJO-1 | M | 8 months | 9.15 kg | Used for ELISA |
| UPJO-2 | M | 12 months | 7.75 kg | Used for mass spectrometric analysis and ELISA |
| UPJO-3 | M | 5 months | 7.6 kg | Used for mass spectrometric analysis and ELISA |
| UPJO-4 | M | 3 months | 6.2 kg | Used for mass spectrometric analysis and ELISA |
| UPJO-5 | M | 3 months | 6.2 kg | Used for mass spectrometric analysis and ELISA |
| UPJO-6 | M | 7 months | No info | Used for mass spectrometric analysis |
| UPJO-7 | M | 3 months | No info | Used for mass spectrometric analysis |

TABLE 1-continued

Control and UPJO patient characteristics

| Sample | Sex | Age | Weight | Notes |
|---|---|---|---|---|
| UPJO-8 | M | 15 months | No info | Used for mass spectrometric analysis |
| UPJO-9 | M | 5 months | 7.5 kg | Used for mass spectrometric analysis and ELISA |
| UPJO-10 | M | 2 months | 4.8 kg | Used for mass spectrometric analysis and ELISA |
| UPJO-11 | M | 8 months | 8.1 kg | Used for mass spectrometric analysis and ELISA |
| UPJO-12 | M | 4 months | 5.9 kg | Used for mass spectrometric analysis and ELISA |
| UPJO-13 | M | 4 months | 6.4 kg | Used for mass spectrometric analysis and ELISA |
| UPJO-14 | M | 2 months | 7.65 kg | Used for mass spectrometric analysis and ELISA |
| UPJO-15 | M | 6 weeks | 5.6 kg | Used for mass spectrometric analysis and ELISA |
| UPJO-16 | M | 10 weeks | 6.8 kg | Used for mass spectrometric analysis and ELISA |
| UPJO-17 | M | 10 weeks | 4.89 kg | Used for mass spectrometric analysis and ELISA |
| UPJO-18 | M | 9 months | 9.45 kg | Used for mass spectrometric analysis and ELISA |
| UPJO-19 | M | 7 months | 10.3 kg | Used for mass spectrometric analysis and ELISA |
| UPJO-20 | M | 12 months | 10.8 kg | Used for mass spectrometric analysis and ELISA |
| UPJO-21 | M | 10 months | 5.5 kg | Used for mass spectrometric analysis |
| UPJO-22 | M | 6 months | 7.6 kg | Used for mass spectrometric analysis and ELISA |

Due to the limited availability, some of the samples were only used for either mass spectrometric analysis or ELISA and have been identified in the notes. We analyzed urine samples using quantitative, label-free mass spectrometry-based proteomics and calculated the average precursor intensities of identified proteins. Subsequently, a two-step selection process was used to identify candidate biomarker proteins that are more likely to be present in UPJO patients and absent in controls, termed UPJO-inherent. In the first step, we identified 171 proteins that were not detected in the majority of the control samples (16/22 samples, or 72.7%). Accordingly, subsequent screening demonstrated that 50 of the 171 proteins were differentially present in at least 11/21 (52.4%) UPJO samples but undetected in control samples.

To further increase the stringency of the screen, we performed an odds ratio analysis to identify the top 10 ranked proteins (FIGS. 1b and 1c, Table 2). NGAL/LCN2 was included in the analysis to compare the UPJO-selectivity of the top 10 ranked proteins to this acknowledged biomarker. LCN2 was present in 6/16 control samples and 5/17 UPJO samples, yielding a low odds ratio (0.8) when compared to the odds ratios of the top 10 proteins (ranging from 6.3-45). Additionally, neither KIM-1 nor cystatin C were detected in our mass spectrometry analysis, potentially due to their low abundance in comparison to the 10 selected proteins, further underscoring that these top 10 proteins may be superior prognostic markers of UPJO.

TABLE 2

Average precursor intensity values of candidate biomarker proteins in control and UPJO patient urine samples.

| | ISLR | QPRT | SPARCL1 | FGG | SPRR3 | BASP1 | PTGR1 | CFH | VCAM1 | FCN2 | LCN2 |
|---|---|---|---|---|---|---|---|---|---|---|---|
| Control-1 | 1.5E+06 | 0 | 0 | 0 | 0 | 0 | 0 | 0 | 0 | 0 | 0 |
| Control-2 | 0 | 0 | 0 | 1.7E+07 | 0 | 0 | 0 | 8.1E+06 | 0 | 0 | 3.7E+06 |
| Control-3 | 0 | 0 | 0 | 0 | 0 | 0 | 0 | 0 | 0 | 0 | 0 |
| Control-4 | 0 | 0 | 0 | 0 | 0 | 0 | 0 | 0 | 0 | 0 | 0 |
| Control-5 | 0 | 0 | 0 | 0 | 0 | 0 | 0 | 0 | 0 | 0 | 0 |
| Control-6 | 0 | 0 | 0 | 0 | 0 | 0 | 0 | 0 | 0 | 0 | 0 |
| Control-7 | 0 | 0 | 0 | 0 | 0 | 0 | 1.1E+06 | 0 | 0 | 0 | 0 |
| Control-8 | 0 | 0 | 0 | 0 | 0 | 0 | 0 | 0 | 0 | 0 | 0 |
| Control-9 | 1 | 0 | 0 | 0 | 0 | 0 | 0 | 0 | 0 | 0 | 0 |
| Control-10 | 0 | 0 | 0 | 0 | 0 | 0 | 0 | 0 | 0 | 0 | 3.4E+06 |
| Control-11 | 0 | 0 | 0 | 0 | 0 | 0 | 0 | 0 | 0 | 1.8E+06 | 0 |
| Control-12 | 0 | 0 | 0 | 0 | 0 | 0 | 0 | 0 | 0 | 1.5E+06 | 0 |
| Control-13 | 0 | 0 | 0 | 0 | 0 | 0 | 0 | 0 | 0 | 0 | 0 |
| Control-14 | 0 | 0 | 0 | 0 | 0 | 3.9E+06 | 0 | 0 | 0 | 0 | 1.8E+06 |
| Control-15 | 0 | 1 | 0 | 0 | 0 | 0 | 0 | 0 | 0 | 0 | 2.7E+06 |
| Control-16 | 0 | 0 | 0 | 0 | 0 | 0 | 0 | 0 | 0 | 0 | 0 |
| Control-17 | 0 | 0 | 4.2E+06 | 0 | 0 | 0 | 0 | 6.6E+06 | 4.7E+06 | 0 | 0 |
| Control-18 | 0 | 0 | 0 | 0 | 0 | 0 | 0 | 0 | 0 | 0 | 0 |
| Control-19 | 0 | 0 | 0 | 0 | 0 | 0 | 1.6E+06 | 0 | 0 | 0 | 3.4E+06 |
| Control-20 | 0 | 5.9E+06 | 0 | 1.2E+07 | 5.2E+06 | 9.7E+06 | 1.0E+07 | 3.1E+06 | 1.3E+07 | 0 | 1.6E+06 |
| Control-21 | 0 | 0 | 0 | 0 | 2.4E+07 | 0 | 0 | 0 | 0 | 3.0E+06 | 0 |
| Control-22 | 0 | 0 | 0 | 0 | 0 | 0 | 0 | 0 | 6.3E+05 | 0 | 0 |
| UPJO-2 | 3.0E+06 | 0 | 1.5E+07 | 4.1E+06 | 0 | 1.0E+07 | 0 | 2.9E+06 | 1.5E+06 | 6.9E+06 | 0 |
| UPJO-3 | 3.3E+06 | 0 | 1 | 2.9E+06 | 0 | 1.8E+06 | 0 | 2.0E+06 | 4.0E+05 | 0 | 0 |
| UPJO-4 | 3.3E+06 | 0 | 5.1E+06 | 0 | 0 | 2.3E+06 | 0 | 1 | 0 | 0 | 0 |
| UPJO-5 | 5.0E+06 | 5.1E+06 | 7.3E+06 | 0 | 2.0E+06 | 3.2E+06 | 0 | 0 | 4.8E+06 | 3.2E+06 | 1.4E+06 |
| UPJO-6 | 0 | 0 | 0 | 3.7E+07 | 4.6E+06 | 8.9E+06 | 2.1E+06 | 2.9E+07 | 0 | 1 | 9.7E+06 |
| UPJO-7 | 0 | 1.3E+06 | 4.7E+06 | 0 | 0 | 3.7E+06 | 3.0E+06 | 0 | 2.5E+06 | 0 | 0 |
| UPJO-8 | 2.1E+06 | 1.4E+06 | 4.8E+06 | 4.9E+06 | 1 | 4.5E+06 | 9.3E+05 | 1 | 4.1E+06 | 0 | 0 |
| UPJO-9 | 4.5E+06 | 0 | 1.0E+07 | 3.0E+06 | 6.9E+06 | 7.7E+06 | 0 | 1.9E+06 | 0 | 3.6E+06 | 0 |
| UPJO-10 | 9.8E+06 | 2.4E+06 | 2.0E+07 | 3.2E+06 | 5.0E+06 | 1.3E+07 | 0 | 5.4E+06 | 5.7E+06 | 1.2E+07 | 0 |
| UPJO-11 | 3.5E+06 | 0 | 9.2E+06 | 6.2E+06 | 1 | 6.1E+06 | 0 | 4.5E+06 | 2.2E+06 | 6.1E+06 | 0 |
| UPJO-12 | 3.2E+06 | 4.3E+06 | 2.5E+07 | 1.1E+07 | 4.9E+06 | 1.4E+07 | 5.1E+06 | 5.8E+06 | 1.1E+07 | 1.6E+07 | 0 |
| UPJO-13 | 0 | 0 | 0 | 0 | 6.4E+06 | 0 | 9.5E+05 | 1.2E+06 | 0 | 0 | 0 |

TABLE 2-continued

Average precursor intensity values of candidate biomarker proteins in control and UPJO patient urine samples.

| | ISLR | QPRT | SPARCL1 | FGG | SPRR3 | BASP1 | PTGR1 | CFH | VCAM1 | FCN2 | LCN2 |
|---|---|---|---|---|---|---|---|---|---|---|---|
| UPJO-14 | 2.8E+06 | 3.6E+06 | 0 | 3.5E+07 | 1.8E+07 | 8.2E+06 | 3.7E+06 | 9.5E+06 | 0 | 0 | 0 |
| UPJO-15 | 2.1E+06 | 6.8E+06 | 1.2E+07 | 1.2E+07 | 0 | 1.3E+07 | 5.8E+06 | 3.3E+06 | 3.7E+06 | 6.6E+06 | 1.8E+06 |
| UPJO-16 | 6.7E+06 | 1.9E+07 | 0 | 2.6E+07 | 3.6E+07 | 1.3E+07 | 8.8E+06 | 5.0E+06 | 3.9E+06 | 0 | 0 |
| UPJO-17 | 3.1E+06 | 4.3E+06 | 0 | 8.7E+06 | 1 | 0 | 2.4E+06 | 1.8E+06 | 0 | 0 | 0 |
| UPJO-18 | 1.8E+06 | 4.4E+06 | 2.3E+07 | 3.3E+07 | 1.6E+07 | 1.8E+06 | 1.2E+07 | 8.6E+06 | 1.1E+07 | 5.6E+06 | 1.0E+07 |
| UPJO-19 | 0 | 0 | 0 | 0 | 5.2E+07 | 0 | 0 | 2.7E+06 | 0 | 3.5E+06 | 0 |
| UPJO-20 | 0 | 0 | 0 | 0 | 0 | 0 | 0 | 0 | 0 | 0 | 0 |
| UPJO-21 | 2.1E+06 | 2.6E+06 | 0 | 9.5E+06 | 1.7E+07 | 3.9E+06 | 3.2E+06 | 2.6E+06 | 0 | 1.4E+06 | 0 |
| UPJO-22 | 0 | 0 | 0 | 0 | 4.5E+07 | 0 | 0 | 0 | 0 | 3.0E+06 | 1.8E+06 |

Values are average precursor intensities denoted as counts per unit time. LCN2 is included for comparative analysis.

Figure 2A:
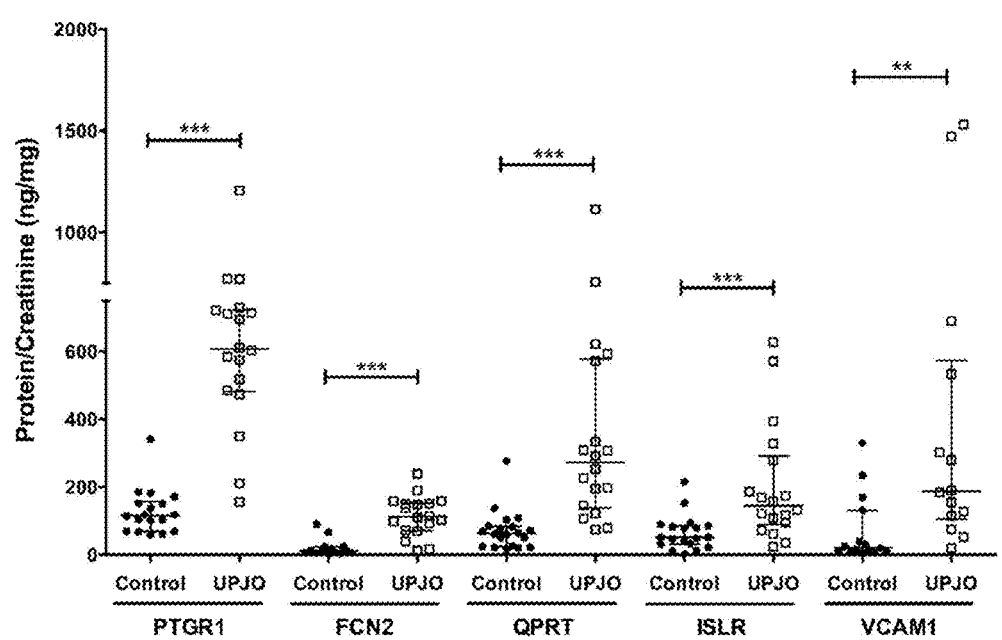
FIG. 2(A-D). Validation of PTGR1, FCN2, QPRT, ISLR and VCAM1 as a panel of UPJO-inherent urinary biomarker proteins. (A) Normalized PTGR1, FCN2, QPRT, ISLR and VCAM1 amounts in control and UPJO samples. Individual protein concentrations (ng/mL) were determined using commercial ELISA kits and normalized to respective urine creatinine concentrations (mg/dL) to obtain protein/creatinine in ng/mg. Data is represented as median (IQR). PTGR1 control (n=18), median (IQR)=118.81 (69.73-152.58); PTGR1 UPJO (n=18), median (IQR)=607.64 (493.13-718.67); FCN2 control (n=18), median (IQR)=11.86 (5.74-23.72); FCN2 UPJO (n=18), median (IQR)=111.82 (77.44-150.73); QPRT control (n=20), median (IQR)=61.30 (25.30-83.56); QPRT UPJO (n=18), median (IQR)=271.79 (157.66-512.80)); ISLR control (n=21), median (IQR)=50.34 (31.43-81.37); ISLR UPJO (n=18), median (IQR)=144.85 (97.78-256.37); VCAM1 control (n=21), median (IQR)=20.38 (10.16-85.42)) and VCAM1 UPJO (n=18), median (IQR)=187.30 (118.49-475.57). Statistical analysis on PTGR1 control and UPJO samples was performed using 2-tailed Student's t test while the rest of the comparative analyses were performed using 2-tailed Mann Whitney test. $p \le 0.01$, *$p \le 0.001$, IQR—Interquartile range. (B) Fold change of medians (UPJO/control) of normalized PTGR1, FCN2, QPRT, ISLR and VCAM1 proteins. (C) Classification of UPJO samples based on the average+3(SD) value of control samples. Average and SD of individual proteins in control samples as determined from ELISA was used to identify UPJO samples with values greater than the average+3(SD) value of respective control samples. Boxes with a "YES" indicate samples with values greater than the average+3(SD) value of control samples, while the boxes with an "x" indicate samples with values smaller than the average+3(SD) value of control samples. Number of positive samples for each protein as well as the number of positive proteins in each sample are enumerated in the table. SD—standard deviation. (D) Summary of percent positive control and UPJO samples. Control and UPJO samples with values greater than the average+3(SD) and average+4(SD) value of respective control samples were enumerated and percent positive samples have been tabulated. SD—standard deviation.
Figure 2B:
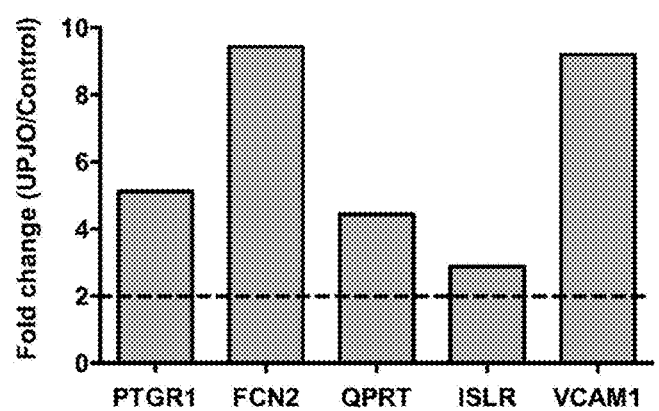

PTGR1, FCN2, QPRT, ISLR and VCAM1 Form a Panel of UPJO-Inherent Biomarker Proteins To determine quantitative values and relative changes, highly sensitive ELISA assays with larger dynamic range were performed for each of the top 10 proteins and normalized to urine creatinine concentrations. The average creatinine concentration in UPJO samples [Ave(SD)-6.11(3.7) mg/dL] was consistently lower than that of the control samples [Ave(SD)-36.42(19.5)mg/dL]. Concentrations of BASP1, FGG and SPRR3 proteins were below the detection limit in all the samples and subsequently excluded from the panel. Similarly, SPARCL1 and CFH were detected in only a few samples and were also removed from further analysis. However, the normalized concentrations of PTGR1, FCN2, QPRT, ISLR and VCAM1 were significantly higher in the UPJO samples (FIG. 2a) with fold-change (UPJO/Control) of the median protein concentrations ranging from 2.9-9.4 (FIG. 2b), further validating their potential as UPJO biomarkers.

To categorize individual control and UPJO samples, we used the average+3(SD) and average+4(SD) values for each of the 5 proteins in the control samples as an arbitrary cutoff to determine the number of individual control and UPJO samples that have values exceeding the cutoff value. Of the 18 UPJO samples, only one sample (UPJO-1) had a value beneath that of the control cutoff value for all 5 proteins, while the remaining 17 samples had at least 1 protein present with a value above the cutoff value (FIG. 2c). Additionally, barring UPJO-5, the remaining 16 samples contain at least 2 proteins at levels above the cutoff value (FIG. 2c). Alternatively, only one control sample (control-16) had PTGR1 and QPRT present at above the respective cutoff value while the remaining controls were below (Table 3).

TABLE 3

Classification of control samples based on the respective average +3(SD) control value Control samples with values greater than the Average +3(SD) value of control samples

| Sample | PTGR1 | FCN2 | QPRT | ISLR | VCAM1 | % Positive proteins |
|---|---|---|---|---|---|---|
| Control-1 | x | x | x | x | x | (0/5) 0% |
| Control-2 | ND | ND | x | x | x | (0/3) 0% |
| Control-3 | x | x | x | x | x | (0/5) 0% |
| Control-4 | x | x | x | x | x | (0/5) 0% |
| Control-5 | x | x | x | x | x | (0/5) 0% |
| Control-6 | x | x | x | x | x | (0/5) 0% |
| Control-7 | x | x | x | x | x | (0/5) 0% |
| Control-8 | x | x | x | x | x | (0/5) 0% |
| Control-9 | x | x | x | x | x | (0/5) 0% |
| Control-10 | x | x | x | x | x | (0/5) 0% |
| Control-11 | x | x | x | x | x | (0/5) 0% |
| Control-13 | x | x | x | x | x | (0/5) 0% |
| Control-14 | ND | ND | ND | x | x | (0/2) 0% |
| Control-15 | x | x | x | x | x | (0/5) 0% |
| Control-16 | YES | x | YES | x | x | (2/5) 40% |
| Control-17 | x | x | x | x | x | (0/5) 0% |
| Control-18 | ND | ND | x | x | x | (0/3) 0% |
| Control-19 | x | x | x | x | x | (0/5) 0% |
| Control-20 | x | x | x | x | x | (0/5) 0% |
| Control-21 | x | x | x | x | x | (0/5) 0% |
| Control-22 | x | x | x | x | x | (0/5) 0% |
| Positive samples (%) | 1/18 (5.56%) | 0/18 (0%) | 1/20 (5%) | 0/21 (0%) | 0/21 (0%) | |

ND—not determined,
SD—standard deviation

Increasing the stringency to average +4(SD) cutoff value eliminated the only positive control sample, while retaining a similar distribution in the UPJO samples (FIG. 2D). Finally, the order of prevalence of the 5 proteins in UPJO samples is PTGR1>FCN2>QPRT>ISLR>VCAM1.

In summary, we identified a panel of urinary biomarker proteins that, when screened collectively, may reliably distinguish between obstructed vs. non-obstructed infants.

Discussion

In this study, we identified a panel of 5 unique proteins that form a UPJO-inherent signature. To achieve this, we minimized variability by selecting a specific cohort of patients who are at the greatest risk and avoided pooling of different age groups that can confound the results. Additionally, only males were included since males are more frequently affected than females (2-3:1). We also established a unique methodology to identify candidate biomarker proteins by choosing proteins that are absent in most control samples rather than choosing proteins that are present in both samples at quantitatively different levels. Although these proteins were detected in some control samples by ELISA analysis, the fold difference was significantly higher with UPJO.

Hydronephrosis can lead to progressive cellular damage due to hypoxia, reactive oxygen species and fibrosis, ultimately resulting in tubular cell death and interstitial inflammation. Considering the multi-dimensional effects of obstruction, it is logical that we identified a diverse biomarker protein panel. Mechanistically, these biomarker proteins are detectable in the urine due to increased release, reduced renal reabsorption or both.

PTGR1 is an enzyme that mediates catabolism of eicosanoids and is highly expressed in kidney tubular cells, cancer cells and aids in cell proliferation and oxidative stress tolerance. Considering the increased oxidative stress on an obstructed kidney, high levels of PTGR1 could be released in the urine due to tubular cell death. Accordingly, PTGR1 was the most prevalent protein in our cohort of UPJO samples (16/18). Similarly, QPRT, an enzyme essential for the synthesis of nicotinamide adenine dinucleotide ($NAD^+$) protects kidneys from acute injury. FCN2, a plasma pattern recognition receptor inhibits epithelial to mesenchymal transition (EMT) of hepatocellular carcinoma by reducing TGF-β signaling. Inhibition of EMT of tubular epithelial cells would be expected to prevent fibrosis in obstructed kidneys and therefore increased FCN2 and QPRT could be early defense mechanisms seen in our cohort of young infants.

Mesenchymal stromal cells (MSCs) in fetal kidney are essential for the differentiation of nephrons and the undifferentiated nature of MSCs is maintained by ISLR, thus the initial observation of ISLR expression in fetal but not adult kidney as well as in our cohort of patients. VCAM1, an inflammation-induced endothelial cell adhesion molecule, is a urinary biomarker for kidney injury in lupus nephritis and in women with preeclampsia.

While our biomarker panel is established by comparing the two extremes of obstruction, confirmed vs. non-obstructed, we are currently collecting samples from patients with equivocal renal scan findings in both sexes to evaluate the panel's utility in a diverse patient population. Overall, this unique screening strategy led to the identification of previously unknown biomarker proteins and is useful in identifying informative biomarker panels for biological samples from many diseases.

Methods

Participants and Urine Samples

De-identified control (n=22) and UPJO (n=22) patients' urine samples were collected with consent from parents and in accordance with an approved IRB protocol (#070-18-EP) from Children's Hospital and Medical Center, Omaha, NE. Frozen urine samples were shipped to UConn Health according to an approved material transfer agreement. Patient cohort consists of males (<2 years) with proven UPJ obstruction (Mag-3 t½>20 min, differential function decrease >10%) undergoing surgical repair. Urine specimens were collected upon catheterization for the Mag-3 study according to standard renogram protocol. Controls are age-matched males undergoing hypospadias repair with no associated renal anomalies.

Creatinine Assay and ELISA

All the experiments were performed according to the manufacturer's instructions. Creatinine levels were determined using creatinine assay kit (KGE005, R&D systems, MN, USA). Human FCN2 (ab213778), CFH (ab213765) and SPARCL1 (ab213826) ELISA kits were purchased from Abcam, MA, USA. Human PTGR1 (366461) and ISLR (152702) kits were purchased from US Biological, MA, USA. Human FGG (LS-F7036), BASP1 (OKCD02007), VCAM1 (KHT0601), QPRT (NBP2-60595) and SPRR3 (MB S2602661) ELISA kits were purchased from LifeSpan Biosciences, WA, USA; Aviva systems biology, CA, USA; Thermo Fisher scientific, MA, USA; Novus Biologicals, CO, USA and MyBioSource, CA, USA, respectively.

Statistical Analyses

GraphPad™ Prism was used to perform statistical analyses. Values from individual experiments were tested for normal distribution by Kolmogorov-Smirnov test. Normally distributed values were compared using 2-tailed Student's t test, while non-normally distributed values were compared using Mann-Whitney U test and significance was determined (*$p \leq 0.05$, $p \leq 0.01$, *$p \leq 0.001$). All the p values from Kolmogorov-Smirnov test, Student's t test and Mann-Whitney U test have been tabulated in the Supplementary File 3.

REFERENCES

1. Kim S Y, Kim M J, Yoon C S, Lee M S, Han K H, Lee M J. Comparison of the reliability of two hydronephrosis grading systems: The Society for Foetal Urology grading system vs. the Onen grading system. *Clin Radiol.* 2013.
2. Piepsz A. Antenatal detection of pelviureteric junction stenosis: main controversies. *Semin Nucl Med.* 2011; 41(1):11-19.
3. Mesrobian H G, Mirza S P. Hydronephrosis: a view from the inside. *Pediatr Clin North Am.* 2012; 59(4):839-851.
4. Conway J J, Maizels M. The "well tempered" diuretic renogram: a standard method to examine the asymptomatic neonate with hydronephrosis or hydroureteronephrosis. A report from combined meetings of The Society for Fetal Urology and members of The Pediatric Nuclear Medicine Council—The Society of Nuclear Medicine. *J Nucl Med.* 1992; 33(11):2047-2051.
5. Wasilewska A, Taranta-Janusz K, Debek W, Zoch-Zwierz W, Kuroczycka-Saniutycz E. KIM-1 and NGAL: new markers of obstructive nephropathy. *Pediatr Nephrol.* 2011; 26(4):579-586.
6. Pavlaki A, Printza N, Farmaki E, et al. The role of urinary NGAL and serum cystatin C in assessing the severity of ureteropelvic junction obstruction in infants. *Pediatr Nephrol.* 2019.
7. Liu K D, Yang W, Anderson A H, et al. Urine neutrophil gelatinase-associated lipocalin levels do not improve risk prediction of progressive chronic kidney disease. *Kidney Int.* 2013; 83(5):909-914.
8. Nielsen S E, Andersen S, Zdunek D, Hess G, Parving H H, Rossing P. Tubular markers do not predict the decline in glomerular filtration rate in type 1 diabetic patients with overt nephropathy. *Kidney Int.* 2011; 79(10):1113-1118.
9. Cost N G, Noh P H, Devarajan P, et al. Urinary NGAL levels correlate with differential renal function in patients with ureteropelvic junction obstruction undergoing pyeloplasty. *J Urol.* 2013; 190(4 Suppl):1462-1467.
10. Urbschat A, Gauer S, Paulus P, et al. Serum and urinary NGAL but not KIM-1 raises in human postrenal AKI. *Eur J Clin Invest.* 2014; 44(7):652-659.
11. Holzscheiter L, Beck C, Rutz S, et al. NGAL, L-FABP, and KIM-1 in comparison to established markers of renal dysfunction. *Clin Chem Lab Med.* 2014; 52(4):537-546.

12. Gerber C, Harel M, Lynch M L, Herbst K W, Ferrer F A, Shapiro L H. Proximal tubule proteins are significantly elevated in bladder urine of patients with ureteropelvic junction obstruction and may represent novel biomarkers: A pilot study. *J Pediatr Urol.* 2016; 12(2):120 e121-127.

13. Drube J, Zurbig P, Schiffer E, et al. Urinary proteome analysis identifies infants but not older children requiring pyeloplasty. *Pediatr Nephrol.* 2010; 25(9):1673-1678.

14. Alizadeh F, Taefnia A M, Haghdani S. Urinary carbohydrate antigen 19-9/creatinine ratio: A non-invasive marker for follow-up of unilateral ureteropelvic junction obstruction in children. *J Pediatr Urol.* 2018; 14(1):62 e61-62 e64.

15. Esmaeili M, Esmaeili M, Ghane F, Alamdaran A. Comparison Between Diuretic Urography (IVP) and Diuretic Renography for Diagnosis of Ureteropelvic Junction Obstruction in Children. *Iran J Pediatr.* 2016; 26(1): e4293.

16. Chevalier R L, Thornhill BA, Forbes M S, Kiley S C. Mechanisms of renal injury and progression of renal disease in congenital obstructive nephropathy. *Pediatr Nephrol.* 2010; 25(4):687-697.

17. Chevalier R L, Thornhill B A, Wolstenholme J T, Kim A. Unilateral ureteral obstruction in early development alters renal growth: dependence on the duration of obstruction. *J Urol.* 1999; 161(1):309-313.

18. Forbes M S, Thornhill B A, Minor J J, Gordon K A, Galarreta C I, Chevalier R L. Fight-or-flight: murine unilateral ureteral obstruction causes extensive proximal tubular degeneration, collecting duct dilatation, and minimal fibrosis. *Am J Physiol Renal Physiol.* 2012; 303(1): F120-129.

19. Sanchez-Rodriguez R, Torres-Mena J E, Quintanar-Jurado V, et al. Ptgr1 expression is regulated by NRF2 in rat hepatocarcinogenesis and promotes cell proliferation and resistance to oxidative stress. *Free radical biology & medicine.* 2017; 102:87-99.

20. Xue L, Zhu Z, Wang Z, et al. Knockdown of prostaglandin reductase 1 (PTGR1) suppresses prostate cancer cell proliferation by inducing cell cycle arrest and apoptosis. *Biosci Trends.* 2016; 10(2):133-139.

21. Poyan Mehr A, Tran M T, Ralto K M, et al. De novo NAD(+) biosynthetic impairment in acute kidney injury in humans. *Nat Med.* 2018; 24(9):1351-1359.

22. Yang G, Liang Y, Zheng T, et al. FCN2 inhibits epithelial-mesenchymal transition-induced metastasis of hepatocellular carcinoma via TGF-beta/Smad signaling. *Cancer letters.* 2016; 378(2):80-86.

23. Klein J, Gonzalez J, Miravete M, et al. Congenital ureteropelvic junction obstruction: human disease and animal models. *Int J Exp Pathol.* 2011; 92(3):168-192.

24. Maeda K, Enomoto A, Hara A, et al. Identification of Meflin as a Potential Marker for Mesenchymal Stromal Cells. *Sci Rep.* 2016; 6:22288.

25. Nagasawa A, Kubota R, Imamura Y, et al. Cloning of the cDNA for a new member of the immunoglobulin superfamily (ISLR) containing leucine-rich repeat (LRR). *Genomics.* 1997; 44(3):273-279.

26. Singh S, Wu T, Xie C, et al. Urine VCAM-1 as a marker of renal pathology activity index in lupus nephritis. *Arthritis Res Ther.* 2012; 14(4):R164.

27. Wang Y, Gu Y, Loyd S, Jia X, Groome L J. Increased urinary levels of podocyte glycoproteins, matrix metallopeptidases, inflammatory cytokines, and kidney injury biomarkers in women with preeclampsia. *Am J Physiol Renal Physiol.* 2015; 309(12):F1009-1017.

Supplemental Methods

Mass Spectrometry Analysis

Total protein content in the urine samples was determined and 1 mL of each sample was mixed with 8 mL of ice-cold acetone and incubated at −20° C. for 1 hour. Samples were centrifuged at 11,000 g for 30 minutes and supernatant was discarded. Pellets were washed with 5 mL of ice-cold acetone and centrifuged at 11,000 g for 30 minutes. Protein pellets were air dried and stored at −80° C. Quantitative label-free mass spectrometry-based proteomics analysis was performed at the UConn Proteomics and Metabolomics Facility.

Urinary Proteomics Sample Preparation

Following protein precipitation and resuspension, an aliquot of each sample containing 100 ug of total protein was removed, dried to completion using a Labconco speedvac concentrator, and reconstituted in 100 μL 0.1 M ammonium bicarbonate in water (pH 8.0). Proteins were then subjected to Cys reduction and alkylation using 5 mM dithiothreitol in 0.1M ammonium bicarbonate (1.5 hours at 37° C.) and 10 mM iodoacetamide in 0.1M ammonium bicarbonate (45 minutes at 37° C. in the dark), respectively. Proteins were digested using sequencing grade modified trypsin (Promega, P/N V5113) at a 1:20 enzyme:protein ratio in a thermal mixer at 37° C. for 16 hours. Proteolysis was quenched by the addition of formic acid to a final pH of 2.5. Tryptic peptides were desalted using Pierce C18 Desalting Spin Columns (P/N 89851) by following manufacturer's instructions. Desalted peptides were dried in a speedvac concentrator, resuspended in 0.1% formic acid in water, and frozen at −20° C. until further analysis.

Quantitative, Label-Free Mass Spectrometry-Based Proteomics Analysis

Tryptic peptides were quantified using a spectrophotometer (Protein A280 mode, Thermo Scientific) and diluted using 0.1% formic acid to provide uniform peptide concentrations across all samples. Peptides were injected into and separated using nanoflow ultra-high performance liquid chromatography and immediately mass analyzed using high resolution tandem mass spectrometry (Thermo Scientific Q Exactive™ HF mass spectrometer). The nanoflow separation implemented a 1 hour linear gradient (Solvent A: 0.1% formic acid in water, Solvent B: 0.1% formic acid in acetonitrile) at 300 nL/min flow rates over a 2 μm, 100 Å, 75 μm×25 cm Easy Spray PepMap™ C18 analytical column (Thermo Scientific) held at 35° C. Eluted peptides were directly ionized using electrospray ionization into the Q Exactive™ HF mass spectrometry which was operated using the following parameters: positive ESI mode, MS1 mass range 300-1800 Da with 60,000 resolution, Top 15 DDA MS/MS acquisition, MS2 resolution of 15,000, 27 NCE and charge state exclusion "on" for unassigned, +1 and >+8 charge states.

All raw files were searched against the Uniprot *Homo sapiens* reference proteome database (accessed 2017 Apr. 22) using Andromeda™ and Maxquant™ software (v1.6.0.1) for peptide identification and label-free quantitation, respectively.[1] The following parameters were used for peptide/protein identification: 1% False Discovery Rate at the protein and peptide levels, variable modifications: oxidation of Met, N-terminal protein acetylation, and N-terminal peptide Gln to pyro Glu, fixed carbamidomethylation on Cys, trypsin cleavage specificity with 2 missed cleavages, 5 amino acids/peptide minimum, and MaxQuant™ LFQ "on".

All other parameters were kept at default values. Search results were uploaded into Scaffold v4.9 (Proteome Software, Inc.) for data visualization and further analysis.

REFERENCES

1. Cox J, Mann M. MaxQuant enables high peptide identification rates, individualized p.p.b.-range mass accuracies and proteome-wide protein quantification. *Nat Biotechnol.* 2008; 26(12): 1367-1372.

We claim:

1. A method for treating ureteropelvic junction obstruction (UPJO) in a subject, wherein the subject is a human child, comprising:
   (a) detecting in a urine sample from the subject one or more proteins selected from the group consisting of Immunoglobulin superfamily containing leucine-rich repeat protein (ISLR); Nicotinate-nucleotide pyrophosphorylase [carboxylating] (QPRT); Prostaglandin reductase 1 (PTGR1); Vascular cell adhesion protein 1 (VCAM1); and Ficolin-2 (FCN2);
   (b) comparing an amount of the one or more proteins in the urine sample to a standard;
   wherein the subject has an increase in the amount of at least one of the one or more proteins in the urine sample above the standard, diagnosing the subject as having UPJO; and
   (c) treating the subject with surgery, endopyelotomy, laparoscopic pyeloplasty, and/or placement of a stent.

2. The method of claim 1, wherein an amount of at least one of the one or more proteins in the urine sample above the standard identifies the subject as at risk of or having an obstructive renal dysfunction resulting from ureteropelvic junction obstruction (UPJO).

3. The method of claim 1, wherein the standard comprises a normal range determined from subjects not having UPJO.

4. The method of claim 1, wherein an amount of at least two, three, four, or all five of the one or more proteins in the urine sample above the standard identifies the subject as having UPJO.

5. The method of claim 1, wherein an amount of PTGR1 in the urine sample above the standard identifies the subject as having UPJO.

6. The method of claim 1, wherein an amount of PTGR1 and FCN2 in the urine sample above the standard identifies the subject as having UPJO.

7. The method of claim 1, wherein an amount of PTGR1, FCN2, and QPRT in the urine sample above the standard identifies the subject as at risk of or having UPJO.

8. The method of claim 1, wherein the subject is under 2 years of age.

9. The method of claim 1, wherein the detecting comprises contacting the urine sample with antibodies that bind to the one or more proteins, and detecting binding of the antibodies to the one or more proteins.

10. The method of claim 9, wherein the detecting comprises an enzyme-linked immunosorbent assay (ELISA).

11. A method for treating UPJO in a subject, comprising;
(a) detecting one or more proteins selected from the group consisting of ISLR, QPRT, PTGR1, VCAM1, and FCN2, in a urine sample from a subject that has undergone treatment for the UPJO, wherein the subject is a human child; and
(b) comparing an amount of the one or more proteins in the urine sample to a standard;
wherein no change or an increase in the amount of the one or more proteins in the urine sample relative to the standard indicates the treatment was ineffective; and
(c) modifying the treatment of the subject, wherein modifying the treatment comprises surgery, endopyelotomy, laparoscopic pyeloplasty, and/or placement of a stent.

* * * * *

SEQUENCE LISTING

```
<160> NUMBER OF SEQ ID NOS: 5

<210> SEQ ID NO 1
<211> LENGTH: 745
<212> TYPE: PRT
<213> ORGANISM: Artificial Sequence
<220> FEATURE:
<223> OTHER INFORMATION: Synthetic

<400> SEQUENCE: 1
```

Met Phe Pro Leu Arg Ala Leu Trp Leu Val Trp Ala Leu Leu Gly Val
1               5                   10                  15

Ala Gly Ser Cys Pro Glu Pro Cys Ala Cys Val Asp Lys Tyr Ala His
            20                  25                  30

Gln Phe Ala Asp Cys Ala Tyr Lys Glu Leu Arg Glu Val Pro Glu Gly
        35                  40                  45

Leu Pro Ala Asn Val Thr Thr Leu Ser Leu Ser Ala Asn Lys Ile Thr
    50                  55                  60

Val Leu Arg Arg Gly Ala Phe Ala Asp Val Thr Gln Val Thr Ser Leu
65                  70                  75                  80

Trp Leu Ala His Asn Glu Val Arg Thr Val Glu Pro Gly Ala Leu Ala
                85                  90                  95

Val Leu Ser Gln Leu Lys Asn Leu Asp Leu Ser His Asn Phe Ile Ser
            100                 105                 110

Ser Phe Pro Trp Ser Asp Leu Arg Asn Leu Ser Ala Leu Gln Leu Leu
        115                 120                 125

Lys Met Asn His Asn Arg Leu Gly Ser Leu Pro Arg Asp Ala Leu Gly
    130                 135                 140

Ala Leu Pro Asp Leu Arg Ser Leu Arg Ile Asn Asn Asn Arg Leu Arg
145                 150                 155                 160

Thr Leu Ala Pro Gly Thr Phe Asp Ala Leu Ser Ala Leu Ser His Leu
                165                 170                 175

Gln Leu Tyr His Asn Pro Phe His Cys Gly Cys Gly Leu Val Trp Leu
            180                 185                 190

Gln Ala Trp Ala Ala Ser Thr Arg Val Ser Leu Pro Glu Pro Asp Ser
        195                 200                 205

Ile Ala Cys Ala Ser Pro Pro Ala Leu Gln Gly Val Pro Val Tyr Arg
    210                 215                 220

Leu Pro Ala Leu Pro Cys Ala Pro Pro Ser Val His Leu Ser Ala Glu
225                 230                 235                 240

Pro Pro Leu Glu Ala Pro Gly Thr Pro Leu Arg Ala Gly Leu Ala Phe
                245                 250                 255

Val Leu His Cys Ile Ala Asp Gly His Pro Thr Pro Arg Leu Gln Trp
            260                 265                 270

Gln Leu Gln Ile Pro Gly Gly Thr Val Val Leu Glu Pro Pro Val Leu
        275                 280                 285

```
Ser Gly Glu Asp Asp Gly Val Gly Ala Glu Gly Glu Gly
    290             295             300

Asp Gly Asp Leu Leu Thr Gln Thr Gln Ala Gln Thr Pro Thr Pro Ala
305             310             315             320

Pro Ala Trp Pro Ala Pro Pro Ala Thr Pro Arg Phe Leu Ala Leu Ala
            325             330             335

Asn Gly Ser Leu Leu Val Pro Leu Leu Ser Ala Lys Glu Ala Gly Val
            340             345             350

Tyr Thr Cys Arg Ala His Asn Glu Leu Gly Ala Asn Ser Thr Ser Ile
            355             360             365

Arg Val Ala Val Ala Ala Thr Gly Pro Pro Lys His Ala Pro Gly Ala
370             375             380

Gly Gly Glu Pro Asp Gly Gln Ala Pro Thr Ser Glu Arg Lys Ser Thr
385             390             395             400

Ala Lys Gly Arg Gly Asn Ser Val Leu Pro Ser Lys Pro Glu Gly Lys
            405             410             415

Ile Lys Gly Gln Gly Leu Ala Lys Val Ser Ile Leu Gly Glu Thr Glu
            420             425             430

Thr Glu Pro Glu Glu Asp Thr Ser Glu Gly Glu Glu Ala Glu Asp Gln
            435             440             445

Ile Leu Ala Asp Pro Ala Glu Glu Gln Arg Cys Gly Asn Gly Asp Pro
450             455             460

Ser Arg Tyr Val Ser Asn His Ala Phe Asn Gln Ser Ala Glu Leu Lys
465             470             475             480

Pro His Val Phe Glu Leu Gly Val Ile Ala Leu Asp Val Ala Glu Arg
            485             490             495

Glu Ala Arg Val Gln Leu Thr Pro Leu Ala Ala Arg Trp Gly Pro Gly
            500             505             510

Pro Gly Gly Ala Gly Gly Ala Pro Arg Pro Gly Arg Arg Pro Leu Arg
            515             520             525

Leu Leu Tyr Leu Cys Pro Ala Gly Gly Ala Ala Val Gln Trp Ser
530             535             540

Arg Val Glu Glu Gly Val Asn Ala Tyr Trp Phe Arg Gly Leu Arg Pro
545             550             555             560

Gly Thr Asn Tyr Ser Val Cys Leu Ala Leu Ala Gly Glu Ala Cys His
            565             570             575

Val Gln Val Val Phe Ser Thr Lys Lys Glu Leu Pro Ser Leu Leu Val
            580             585             590

Ile Val Ala Val Ser Val Phe Leu Leu Val Leu Ala Thr Val Pro Leu
            595             600             605

Leu Gly Ala Ala Cys Cys His Leu Leu Ala Lys His Pro Gly Lys Pro
610             615             620

Tyr Arg Leu Ile Leu Arg Pro Gln Ala Pro Asp Pro Met Glu Lys Arg
625             630             635             640

Ile Ala Ala Asp Phe Asp Pro Arg Ala Ser Tyr Leu Glu Ser Glu Lys
            645             650             655

Ser Tyr Pro Ala Gly Gly Glu Ala Gly Gly Glu Glu Pro Glu Asp Val
            660             665             670

Gln Gly Glu Gly Leu Asp Glu Asp Ala Glu Gln Gly Asp Pro Ser Gly
            675             680             685

Asp Leu Gln Arg Glu Glu Ser Leu Ala Ala Cys Ser Leu Val Glu Ser
690             695             700
```

```
Gln Ser Lys Ala Asn Gln Glu Glu Phe Glu Ala Gly Ser Glu Tyr Ser
705                 710                 715                 720

Asp Arg Leu Pro Leu Gly Ala Glu Ala Val Asn Ile Ala Gln Glu Ile
                725                 730                 735

Asn Gly Asn Tyr Arg Gln Thr Ala Gly
                740                 745

<210> SEQ ID NO 2
<211> LENGTH: 297
<212> TYPE: PRT
<213> ORGANISM: Artificial Sequence
<220> FEATURE:
<223> OTHER INFORMATION: Synthetic

<400> SEQUENCE: 2

Met Asp Ala Glu Gly Leu Ala Leu Leu Pro Pro Val Thr Leu Ala
1               5                   10                  15

Ala Leu Val Asp Ser Trp Leu Arg Glu Asp Cys Pro Gly Leu Asn Tyr
                20                  25                  30

Ala Ala Leu Val Ser Gly Ala Gly Pro Ser Gln Ala Ala Leu Trp Ala
                35                  40                  45

Lys Ser Pro Gly Val Leu Ala Gly Gln Pro Phe Phe Asp Ala Ile Phe
50                  55                  60

Thr Gln Leu Asn Cys Gln Val Ser Trp Phe Leu Pro Glu Gly Ser Lys
65                  70                  75                  80

Leu Val Pro Val Ala Arg Val Ala Glu Val Arg Gly Pro Ala His Cys
                85                  90                  95

Leu Leu Leu Gly Glu Arg Val Ala Leu Asn Thr Leu Ala Arg Cys Ser
                100                 105                 110

Gly Ile Ala Ser Ala Ala Ala Ala Val Glu Ala Ala Arg Gly Ala
                115                 120                 125

Gly Trp Thr Gly His Val Ala Gly Thr Arg Lys Thr Thr Pro Gly Phe
    130                 135                 140

Arg Leu Val Glu Lys Tyr Gly Leu Leu Val Gly Gly Ala Ala Ser His
145                 150                 155                 160

Arg Tyr Asp Leu Gly Gly Leu Val Met Val Lys Asp Asn His Val Val
                165                 170                 175

Ala Ala Gly Gly Val Glu Lys Ala Val Arg Ala Ala Arg Gln Ala Ala
                180                 185                 190

Asp Phe Thr Leu Lys Val Glu Val Glu Cys Ser Ser Leu Gln Glu Ala
                195                 200                 205

Val Gln Ala Ala Glu Ala Gly Ala Asp Leu Val Leu Leu Asp Asn Phe
    210                 215                 220

Lys Pro Glu Glu Leu His Pro Thr Ala Thr Val Leu Lys Ala Gln Phe
225                 230                 235                 240

Pro Ser Val Ala Val Glu Ala Ser Gly Gly Ile Thr Leu Asp Asn Leu
                245                 250                 255

Pro Gln Phe Cys Gly Pro His Ile Asp Val Ile Ser Met Gly Met Leu
                260                 265                 270

Thr Gln Ala Ala Pro Ala Leu Asp Phe Ser Leu Lys Leu Phe Ala Lys
                275                 280                 285

Glu Val Ala Pro Val Pro Lys Ile His
                290                 295

<210> SEQ ID NO 3
<211> LENGTH: 329
```

<212> TYPE: PRT
<213> ORGANISM: Artificial Sequence
<220> FEATURE:
<223> OTHER INFORMATION: Synthetic

<400> SEQUENCE: 3

```
Met Val Arg Thr Lys Thr Trp Thr Leu Lys Lys His Phe Val Gly Tyr
1               5                   10                  15

Pro Thr Asn Ser Asp Phe Glu Leu Lys Thr Ala Glu Leu Pro Pro Leu
            20                  25                  30

Lys Asn Gly Glu Val Leu Leu Glu Ala Leu Phe Leu Thr Val Asp Pro
        35                  40                  45

Tyr Met Arg Val Ala Ala Lys Arg Leu Lys Glu Gly Asp Thr Met Met
    50                  55                  60

Gly Gln Gln Val Ala Lys Val Glu Ser Lys Asn Val Ala Leu Pro
65                  70                  75                  80

Lys Gly Thr Ile Val Leu Ala Ser Pro Gly Trp Thr Thr His Ser Ile
                85                  90                  95

Ser Asp Gly Lys Asp Leu Glu Lys Leu Leu Thr Glu Trp Pro Asp Thr
            100                 105                 110

Ile Pro Leu Ser Leu Ala Leu Gly Thr Val Gly Met Pro Gly Leu Thr
        115                 120                 125

Ala Tyr Phe Gly Leu Leu Glu Ile Cys Gly Val Lys Gly Gly Glu Thr
    130                 135                 140

Val Met Val Asn Ala Ala Ala Gly Ala Val Gly Ser Val Val Gly Gln
145                 150                 155                 160

Ile Ala Lys Leu Lys Gly Cys Lys Val Val Gly Ala Val Gly Ser Asp
                165                 170                 175

Glu Lys Val Ala Tyr Leu Gln Lys Leu Gly Phe Asp Val Val Phe Asn
            180                 185                 190

Tyr Lys Thr Val Glu Ser Leu Glu Gly Thr Leu Lys Lys Ala Ser Pro
        195                 200                 205

Asp Gly Tyr Asp Cys Tyr Phe Asp Asn Val Gly Gly Glu Phe Ser Asn
    210                 215                 220

Thr Val Ile Gly Gln Met Lys Lys Phe Gly Arg Ile Ala Ile Cys Gly
225                 230                 235                 240

Ala Ile Ser Thr Tyr Asn Arg Thr Gly Pro Leu Pro Pro Gly Pro Pro
                245                 250                 255

Pro Glu Ile Val Ile Tyr Gln Glu Leu Arg Met Glu Ala Phe Val Val
            260                 265                 270

Tyr Arg Trp Gln Gly Asp Ala Arg Gln Lys Ala Leu Lys Asp Leu Leu
        275                 280                 285

Lys Trp Val Leu Glu Gly Lys Ile Gln Tyr Lys Glu Tyr Ile Ile Glu
    290                 295                 300

Gly Phe Glu Asn Met Pro Ala Ala Phe Met Gly Met Leu Lys Gly Asp
305                 310                 315                 320

Asn Leu Gly Lys Thr Ile Val Lys Ala
                325
```

<210> SEQ ID NO 4
<211> LENGTH: 739
<212> TYPE: PRT
<213> ORGANISM: Artificial Sequence
<220> FEATURE:
<223> OTHER INFORMATION: Synthetic

<400> SEQUENCE: 4

```
Met Pro Gly Lys Met Val Ile Leu Gly Ala Ser Asn Ile Leu Trp
1               5                   10                  15

Ile Met Phe Ala Ala Ser Gln Ala Phe Lys Ile Glu Thr Thr Pro Glu
                20                  25                  30

Ser Arg Tyr Leu Ala Gln Ile Gly Asp Ser Val Ser Leu Thr Cys Ser
            35                  40                  45

Thr Thr Gly Cys Glu Ser Pro Phe Phe Ser Trp Arg Thr Gln Ile Asp
        50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
            115                 120                 125

Ala Gly Lys Pro Ile Thr Val Lys Cys Ser Val Ala Asp Val Tyr Pro
            130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
                180                 185                 190

Leu Val Cys Arg Ala Lys Leu His Ile Asp Glu Met Asp Ser Val Pro
            195                 200                 205

Thr Val Arg Gln Ala Val Lys Glu Leu Gln Val Tyr Ile Ser Pro Lys
210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
            275                 280                 285

Tyr Val Cys Glu Gly Val Asn Leu Ile Gly Lys Asn Arg Lys Glu Val
            290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
            325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
            355                 360                 365

Thr Leu Ser Pro Val Ser Phe Glu Asn Glu His Ser Tyr Leu Cys Thr
            370                 375                 380

Val Thr Cys Gly His Lys Lys Leu Glu Lys Gly Ile Gln Val Glu Leu
385                 390                 395                 400

Tyr Ser Phe Pro Arg Asp Pro Gly Ile Glu Met Ser Gly Gly Leu Val
                405                 410                 415
```

```
Asn Gly Ser Ser Val Thr Val Ser Cys Lys Val Pro Ser Val Tyr Pro
                420                 425                 430

Leu Asp Arg Leu Glu Ile Glu Leu Leu Lys Gly Glu Thr Ile Leu Glu
            435                 440                 445

Asn Ile Glu Phe Leu Glu Asp Thr Asp Met Lys Ser Leu Glu Asn Lys
        450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510

Asp Thr Thr Val Leu Val Ser Pro Ser Ser Ile Leu Glu Glu Gly Ser
        515                 520                 525

Ser Val Asn Met Thr Cys Leu Ser Gln Gly Phe Pro Ala Pro Lys Ile
530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
        595                 600                 605

Pro Ser Glu Ser Val Lys Glu Gly Asp Thr Val Ile Ile Ser Cys Thr
610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
            660                 665                 670

Lys Val Gly Ser Gln Leu Arg Ser Leu Thr Leu Asp Val Gln Gly Arg
        675                 680                 685

Glu Asn Asn Lys Asp Tyr Phe Ser Pro Glu Leu Leu Val Leu Tyr Phe
690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 5
<211> LENGTH: 313
<212> TYPE: PRT
<213> ORGANISM: Artificial Sequence
<220> FEATURE:
<223> OTHER INFORMATION: Synthetic

<400> SEQUENCE: 5

Met Glu Leu Asp Arg Ala Val Gly Val Leu Gly Ala Ala Thr Leu Leu
1               5                   10                  15

Leu Ser Phe Leu Gly Met Ala Trp Ala Leu Gln Ala Ala Asp Thr Cys
                20                  25                  30

Pro Glu Val Lys Met Val Gly Leu Glu Gly Ser Asp Lys Leu Thr Ile
```

-continued

```
                35                  40                  45
Leu Arg Gly Cys Pro Gly Leu Pro Gly Ala Pro Gly Pro Lys Gly Glu
    50                  55                  60

Ala Gly Thr Asn Gly Lys Arg Gly Glu Arg Gly Pro Pro Gly Pro Pro
65                  70                  75                  80

Gly Lys Ala Gly Pro Pro Gly Pro Asn Gly Ala Pro Gly Glu Pro Gln
                85                  90                  95

Pro Cys Leu Thr Gly Pro Arg Thr Cys Lys Asp Leu Leu Asp Arg Gly
            100                 105                 110

His Phe Leu Ser Gly Trp His Thr Ile Tyr Leu Pro Asp Cys Arg Pro
            115                 120                 125

Leu Thr Val Leu Cys Asp Met Asp Thr Asp Gly Gly Gly Trp Thr Val
            130                 135                 140

Phe Gln Arg Arg Val Asp Gly Ser Val Asp Phe Tyr Arg Asp Trp Ala
145                 150                 155                 160

Thr Tyr Lys Gln Gly Phe Gly Ser Arg Leu Gly Glu Phe Trp Leu Gly
                165                 170                 175

Asn Asp Asn Ile His Ala Leu Thr Ala Gln Gly Thr Ser Glu Leu Arg
                180                 185                 190

Val Asp Leu Val Asp Phe Glu Asp Asn Tyr Gln Phe Ala Lys Tyr Arg
            195                 200                 205

Ser Phe Lys Val Ala Asp Glu Ala Glu Lys Tyr Asn Leu Val Leu Gly
    210                 215                 220

Ala Phe Val Glu Gly Ser Ala Gly Asp Ser Leu Thr Phe His Asn Asn
225                 230                 235                 240

Gln Ser Phe Ser Thr Lys Asp Gln Asp Asn Asp Leu Asn Thr Gly Asn
                245                 250                 255

Cys Ala Val Met Phe Gln Gly Ala Trp Trp Tyr Lys Asn Cys His Val
            260                 265                 270

Ser Asn Leu Asn Gly Arg Tyr Leu Arg Gly Thr His Gly Ser Phe Ala
            275                 280                 285

Asn Gly Ile Asn Trp Lys Ser Gly Lys Gly Tyr Asn Tyr Ser Tyr Lys
    290                 295                 300

Val Ser Glu Met Lys Val Arg Pro Ala
305                 310
```